United States Patent
Cao et al.

(10) Patent No.: US 12,397,163 B2
(45) Date of Patent: *Aug. 26, 2025

(54) HIS-PURKINJE SYSTEM CAPTURE DETECTION

(71) Applicant: Medtronic, Inc., Minneapolis, MN (US)

(72) Inventors: Jian Cao, Shoreview, MN (US); Wade M. Demmer, Coon Rapids, MN (US); Maureen E. Lybarger, New Brighton, MN (US); Elizabeth A Mattson, Eagan, MN (US); Todd J. Sheldon, North Oaks, MN (US); Zhongping Yang, Woodbury, MN (US); Xiaohong Zhou, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 94 days.

This patent is subject to a terminal disclaimer.

(21) Appl. No.: 18/167,795

(22) Filed: Feb. 10, 2023

(65) Prior Publication Data

US 2023/0181911 A1   Jun. 15, 2023

Related U.S. Application Data

(63) Continuation of application No. 16/901,110, filed on Jun. 15, 2020, now Pat. No. 11,607,550.

(60) Provisional application No. 62/866,037, filed on Jun. 25, 2019.

(51) Int. Cl.
*A61N 1/37* (2006.01)
*A61N 1/365* (2006.01)

(52) U.S. Cl.
CPC ....... *A61N 1/36507* (2013.01); *A61N 1/3704* (2013.01); *A61N 1/3706* (2013.01); *A61N 1/3714* (2013.01)

(58) Field of Classification Search
CPC ....... A61N 1/365; A61N 1/371; A61N 1/3712
See application file for complete search history.

(56) References Cited

U.S. PATENT DOCUMENTS

| | | | |
|---|---|---|---|
| 6,148,234 | A | 11/2000 | Struble |
| 6,353,761 | B1 | 3/2002 | Conley et al. |
| 6,609,027 | B2 | 8/2003 | Kroll et al. |

(Continued)

FOREIGN PATENT DOCUMENTS

| | | |
|---|---|---|
| EP | 1234597 A2 | 8/2002 |
| WO | 2019089510 A1 | 5/2019 |

OTHER PUBLICATIONS

Saini et al, Novel Method for Assessment of His Bundle Pacing Morphology Using Near Field and Far Field Device Electrograms, retrieved at: https://www.ahajournals.org/doi/10.1161/CIRCEP.118.006878, Feb. 1, 2019, 24 pages.

(Continued)

*Primary Examiner* — Allen Porter

(57) ABSTRACT

A medical device is configured to sense a cardiac electrical signal and determine from the cardiac electrical signal at least one of a maximum peak amplitude of a positive slope of the cardiac electrical signal and a maximum peak time interval from a pacing pulse to the maximum peak amplitude. The device is configured to determine a capture type of the pacing pulse based on at least one or both of the maximum peak amplitude and the maximum peak time interval.

18 Claims, 12 Drawing Sheets

(56) References Cited

U.S. PATENT DOCUMENTS

| | | | |
|---|---|---|---|
| 6,768,924 B2 | 7/2004 | Ding et al. |
| 7,184,815 B2 | 2/2007 | Kim et al. |
| 7,412,287 B2 | 8/2008 | Yonce et al. |
| 8,527,050 B2 | 9/2013 | Stadler et al. |
| 8,565,865 B2 | 10/2013 | Belk et al. |
| 8,761,880 B2 | 6/2014 | Maskara et al. |
| 9,002,454 B2 | 4/2015 | Ghosh et al. |
| 9,168,382 B2 | 10/2015 | Shuros et al. |
| 9,227,073 B2 | 1/2016 | Bohn et al. |
| 9,789,319 B2 | 10/2017 | Sambelashvili |
| 10,881,862 B2 | 1/2021 | Ghosh |
| 11,027,136 B2 | 6/2021 | Mangual-Soto et al. |
| 2008/0119905 A1 | 5/2008 | Bohn et al. |
| 2011/0264158 A1 | 10/2011 | Dong et al. |
| 2012/0101542 A1 | 4/2012 | Arcot-Krishnamurthy et al. |
| 2013/0030491 A1 | 1/2013 | Stadler et al. |
| 2014/0107724 A1 | 4/2014 | Shuros et al. |
| 2019/0022378 A1 | 1/2019 | Prillinger et al. |
| 2019/0083800 A1 | 3/2019 | Yang et al. |
| 2019/0111265 A1 | 4/2019 | Zhou |
| 2019/0111270 A1 | 4/2019 | Zhou |
| 2019/0126049 A1 | 5/2019 | Casavant et al. |
| 2019/0134404 A1 | 5/2019 | Sheldon et al. |
| 2019/0134405 A1 | 5/2019 | Sheldon et al. |
| 2019/0192860 A1 | 6/2019 | Ghosh et al. |
| 2020/0353266 A1 | 11/2020 | Min et al. |

OTHER PUBLICATIONS

Adachi et al, "QRS Complex Widening Due to Loss of Left Bundle Branch Capture: Pitfall of Para-Hisian Pacing", Journal of Interventional Cardiac Electrophysiology 2009, 4 pages.

Deshmukh et al., "Permanent, Direct HIS-Bundle Pacing: A Novel Approach to Cardiac Pacing in Patients with Normal HIS-Purkinje Activation", Circulation, American Heart Association, Inc., vol. 101, No. 8, Feb. 29, 2000, pages.

Dandamudi et al., "How to Perform Permanent His Bundle Pacing in Routine Clinical Practice", 2016, Heart Rhythm Society, 5 pages.

Yuyun et al., "HIS Bundle Pacing: State of the Art", US Cardiology, vol. 12, No. 1, Jan. 2017, 10 pages.

(PCT/US2020/039102) PCT Notification of Transmittal of the International Search Report and the Written Opinion of the International Searching Authority, Mailed Oct. 5, 2020, 11 pages.

"Office Action Issued in Chinese Patent Application No. 202080043753.4", Mailed Date: May 23, 2025, 17 Pages.

HIS-PURKINJE SYSTEM CAPTURE DETECTION

REFERENCE TO RELATED APPLICATION

This application is a Continuation of U.S. patent application Ser. No. 16/901,110, filed on Jun. 15, 2020, which claims the benefit of provisional U.S. Patent Application No. 62/866,037, filed on Jun. 25, 2019, entitled "His Bundle Capture Detection," the content of both of which incorporated herein by reference in its entirety.

TECHNICAL FIELD

This disclosure relates to a medical device and method for determining the type of cardiac capture following delivery of a pacing pulse.

BACKGROUND

During normal sinus rhythm (NSR), the heartbeat is regulated by electrical signals produced by the sino-atrial (SA) node located in the right atrial wall. Each intrinsic atrial depolarization signal produced by the SA node spreads across the atria, causing the depolarization and contraction of the atria, and arrives at the atrioventricular (AV) node. The AV node responds by propagating a ventricular depolarization signal through the Purkinje of His (or "His bundle") of the ventricular septum and thereafter to the Purkinje branches and the Purkinje muscle fibers of the right and left ventricles. This native conduction system including the His bundle, right and left branches (sometimes referred to as the right and left bundle branches) and the Purkinje fibers may be referred to as the "His-Purkinje conduction system" or "His-Purkinje system."

Patients with a conduction system abnormality, e.g., poor AV node conduction, poor SA node function, or other conduction abnormalities, may receive a pacemaker to restore a more normal heart rhythm and AV synchrony. Ventricular pacing may be performed to maintain the ventricular rate in a patient having atrioventricular conduction abnormalities. A single chamber ventricular pacemaker may be coupled to a transvenous ventricular lead carrying electrodes placed in the right ventricle, e.g., in the right ventricular apex. The pacemaker itself is generally implanted in a subcutaneous pocket with the transvenous ventricular lead tunneled to the subcutaneous pocket. Intracardiac pacemakers have been introduced or proposed for implantation entirely within a patient's heart, eliminating the need for transvenous leads. An intracardiac pacemaker may provide sensing and pacing from within a chamber of the patient's heart, e.g., from within the right ventricle in a patient having AV conduction block or other conduction abnormalities to provide ventricular rate support.

Dual chamber pacemakers are available which include a transvenous atrial lead carrying electrodes which are placed in the right atrium and a transvenous ventricular lead carrying electrodes that are placed in the right ventricle via the right atrium. A dual chamber pacemaker senses atrial electrical signals and ventricular electrical signals and can provide both atrial pacing and ventricular pacing as needed to promote a normal atrial and ventricular rhythm and promote AV synchrony when SA and/or AV node or other conduction abnormalities are present.

Cardiac pacing of the His-Purkinje system has been proposed to provide ventricular pacing along the heart's native His-Purkinje conduction system. Chronic ventricular pacing via electrodes at or near the right ventricular apex may be associated with increased risk of atrial fibrillation or heart failure. Alternative pacing sites have been investigated or proposed, such as pacing the at or near the His bundle. Pacing the ventricles via the His-Purkinje system allows recruitment along the heart's natural conduction system and is hypothesized to promote more physiologically normal cardiac activation than other pacing sites, such as the ventricular apex.

SUMMARY

The techniques of this disclosure generally relate to determining the type of cardiac capture achieved by cardiac pacing pulses delivered via pacing electrodes positioned to pace the His-Purkinje system. The pacing and sensing electrodes may be carried by a lead, e.g., a transvenous endocardial lead. In other examples, the pacing and sensing electrodes may be housing-based electrodes along the housing of a leadless pacemaker. Among the types of capture that may be achieved during His-Purkinje system pacing are selective His-Purkinje system capture during which only the His-Purkinje system is captured, non-selective His-Purkinje system capture during which both portions of the His-Purkinje system and the ventricular myocardium are captured, ventricular myocardial capture only without capture of the His-Purkinje system, and loss of ventricular capture. The type of capture may depend on the location of the electrodes relative to the His-Purkinje system, the pacing pulse energy and other factors. A medical device operating according to the techniques disclosed herein may determine the type of capture following a pacing pulse and determine various capture thresholds for different types of capture such as selective His-Purkinje system capture and ventricular myocardial capture. The medical device may respond to determination of the capture type by adjusting a pacing pulse control parameter such as pacing pulse amplitude or performing a capture threshold search. The medical device may be configured to monitor for capture during cardiac pacing delivered to the His-Purkinje system to detect a change in capture type and provide an appropriate response.

In one example, the disclosure provides a medical device including a sensing circuit configured to sense a cardiac electrical signal. The device may include a therapy delivery circuit configured to generate pacing pulses. The device includes a control circuit configured to determine one or both of the maximum peak amplitude of a positive slope of the cardiac electrical signal and the maximum peak time interval from a pacing pulse to the maximum peak amplitude of the positive slope. The device is configured to determine the type of capture by the pacing pulse as being either non-selective His-Purkinje system capture or ventricular myocardial capture based one or both of the maximum peak amplitude and the maximum peak time interval.

In another example, the disclosure provides a method performed by a medical device including sensing a cardiac electrical signal and determining one or both of the maximum peak amplitude of a positive slope of the cardiac electrical signal and the maximum peak time interval from a pacing pulse to the maximum peak amplitude of the positive slope. The method further includes determining the type of capture achieved by the pacing pulse as being either non-selective His-Purkinje system capture or only ventricular myocardial capture based on one or both of the maximum peak amplitude and the maximum peak time interval.

In yet another example, the disclosure provides a non-transitory, computer-readable storage medium comprising a set of instructions which, when executed by a control circuit of a medical device, cause the medical device to sense a cardiac electrical signal and determine one or both of the maximum peak amplitude of a positive slope of the cardiac electrical signal and the maximum peak time interval from a pacing pulse to the maximum peak amplitude of the positive slope. The instructions further cause the device to determine the type of capture achieved by the pacing pulse as being either non-selective His-Purkinje system capture or ventricular myocardial capture only based on one or both of the maximum peak amplitude and the maximum peak time interval.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1A:
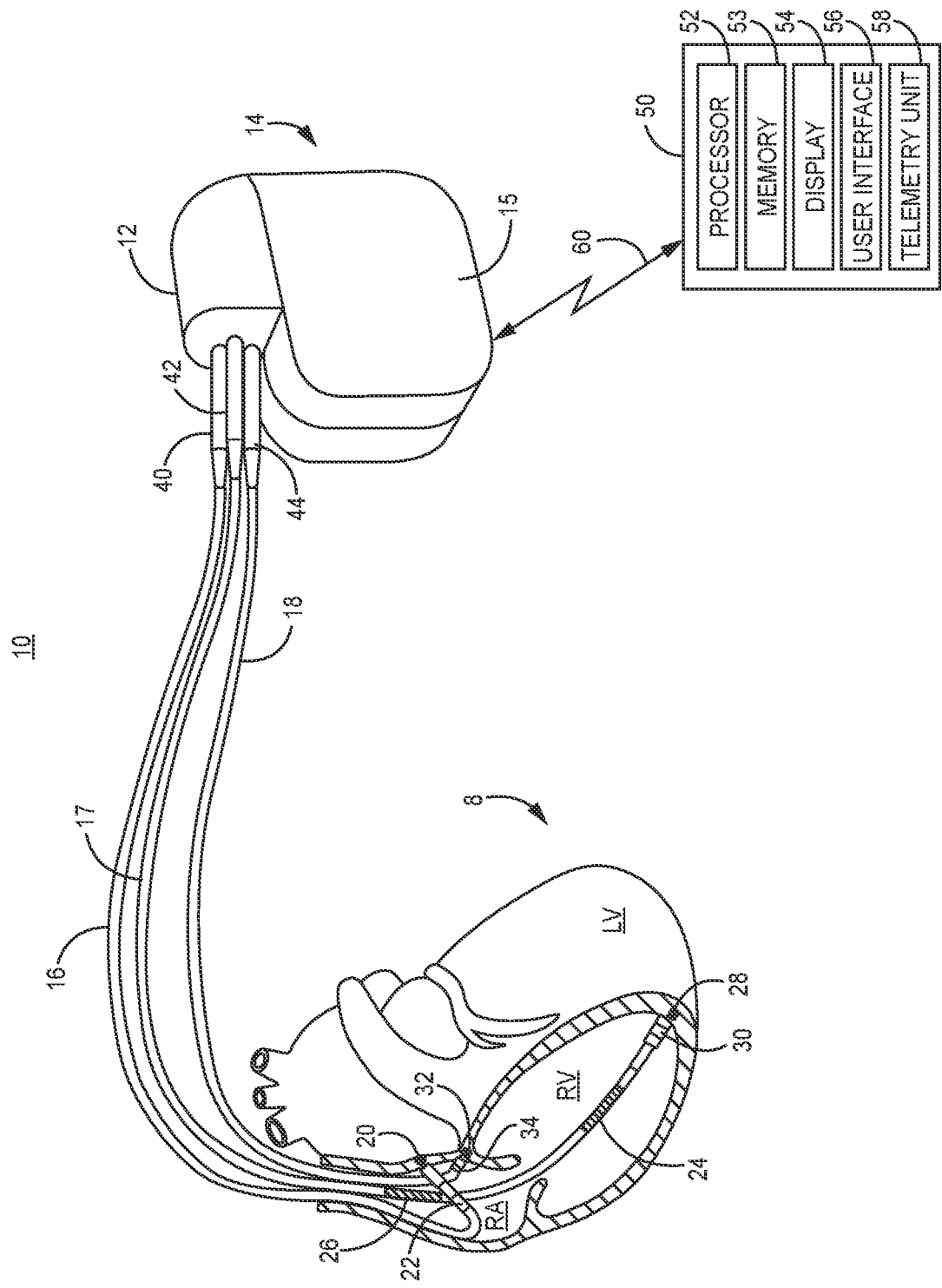
FIG. 1A is a conceptual diagram of a medical device system capable of delivering His-Purkinje system pacing and sensing cardiac electrical signals.

Examples of a medical device capable of generating pacing pulses for delivery to the His-Purkinje conduction system of a patient's heart are described herein. The medical device is configured to detect the type of cardiac capture that occurs following a generated pacing pulse according to the presently disclosed techniques. A cardiac tissue is "captured" by a pacing pulse having sufficient electrical energy to cause depolarization of the cardiac tissue at the pacing site, causing an electrical "evoked response," and subsequent mechanical contraction of the heart chamber. In order to effectively capture and pace the heart to achieve a desired therapeutic effect, cardiac pacing pulses need to have a pulse energy that is equal to or greater than the capture threshold of the cardiac tissue at the pacing site. A pacing capture threshold test may be performed to determine the minimum pacing pulse amplitude for a given pacing pulse width (or vice versa) that captures the heart chamber. Determination of the capture threshold enables proper programming of the pacing pulse amplitude and pulse width to promote effective pacing and avoid loss of capture. Capture monitoring by the pacemaker during ongoing pacing pulse delivery according to a pacing therapy allows automatic adjustments to the pacing pulse amplitude and/or pulse width to a suprathreshold value when loss of capture or a change in capture type is detected.

As used herein, the term "His-Purkinje" e.g., used to refer to "His-Purkinje pacing," "His-Purkinje pacing pulses," "His-Purkinje capture," etc., may refer collectively to the His-Purkinje conduction system, which includes the His bundle, right and left-Purkinje branches and the Purkinje fibers, such that "His-Purkinje pacing" may refer generally to pacing anywhere along the His-Purkinje conduction system, "His-Purkinje pacing pulses" may be delivered anywhere along the His-Purkinje conduction system, and "His-Purkinje capture" may refer to capture of the His-Purkinje conduction system, which may be capture at or inferior to the His bundle, and is also referred to herein as "His-Purkinje system capture." When pacing pulses are delivered by electrodes positioned in the heart to pace the His-Purkinje conduction system it is possible to capture only the His-Purkinje system, capture both the His-Purkinje system and surrounding ventricular myocardium, or capture the surrounding ventricular myocardium without capturing the His-Purkinje system. Capture of only the His-Purkinje system is referred to herein as "selective" His-Purkinje system (SHP) capture. Capture of the His-Purkinje system and surrounding ventricular myocardial tissue is referred to herein as "non-selective" His-Purkinje system (NSHP) capture. Capture of the surrounding ventricular myocardium without capturing the His-Purkinje system is referred to as ventricular myocardial (VM) capture. When the pacing pulse energy is below both the His-Purkinje system capture threshold and the VM capture threshold, a loss of capture occurs. Determination of which type of capture is occurring in response to a His-Purkinje pacing pulse intended to capture the anywhere along the His-Purkinje system and determination of the His-Purkinje capture threshold allows for providing selective or non-selective capture of the His-Purkinje system, as desired, in order to achieve ventricular pacing along the native His-Purkinje system.

FIG. 1 is a conceptual diagram of a medical device system 10 capable of pacing and sensing in a patient's heart 8. The system 10 includes implantable medical device (IMD) 14 coupled to a patient's heart 8 via transvenous electrical leads 16, 17 and 18. IMD 14 is shown as a dual chamber device capable of delivering cardiac pacing pulses and sensing cardiac electrical signals in the right atrium (RA) and in the right ventricle (RV). Housing 15 encloses internal circuitry corresponding to the various circuits and components described in conjunction with FIG. 3 below, for sensing cardiac signals from heart 8, detecting arrhythmias, controlling therapy delivery and monitoring for capture type using the techniques disclosed herein.

IMD 14 includes a connector block 12 that may be configured to receive the proximal ends of a RA lead 16, an optional RV lead 17 and a His pacing and sensing lead 18, which are advanced transvenously for positioning electrodes for sensing and stimulation in the atria and ventricles. RA lead 16 is positioned such that its distal end is in the vicinity of the right atrium and the superior vena cava. RA lead 16 is equipped with pacing and sensing electrodes 20 and 22, shown as a tip electrode 20 and a ring electrode 22 spaced proximally from tip electrode 20. The electrodes 20 and 22 provide sensing and pacing in the right atrium and are each connected to a respective insulated conductor extending within the elongated body of RA lead 16. Each insulated conductor is coupled at its proximal end to a connector carried by proximal lead connector 40.

His pacing and sensing lead 18 may be advanced within the right atrium to position electrodes 32 and 34 for pacing and sensing in the vicinity of the His-Purkinje system, e.g., at or near the His bundle, from a right atrial approach, as shown. His lead tip electrode 32 may be a helical electrode that is advanced into the inferior end of the interatrial septum, beneath the AV node and near the tricuspid valve annulus to position tip electrode 32 in or proximate to the His bundle. A ring electrode 34 spaced proximally from tip electrode 32 may be used as the return electrode with the cathode tip electrode 32 for pacing the right and left ventricles via the native His-Purkinje system.

An intracardiac electrogram (EGM) signal may be produced by cardiac electrical signal sensing circuitry included in IMD 14 from the cardiac electrical signal obtained using the tip electrode 32 and ring electrode 34 of His pacing and sensing lead 18 and received by the sensing circuitry. As described below, the EGM signal produced from the cardiac electrical signal received via His pacing and sensing lead 18 is referred to herein as a "near field His-Purkinje signal" and may be used for detecting capture of the His-Purkinje system and discriminating between SHP capture, NSHP capture, VM capture and loss of capture. The electrodes 32 and 34 are coupled to respective insulated conductors extending within the elongated body of His pacing and sensing lead 18, which provide electrical connection to the proximal lead connector 44 coupled to connector block 12.

In some examples, IMD 14 may optionally be coupled to RV lead 17 for positioning electrodes within the RV for sensing RV cardiac signals and delivering pacing or shocking pulses in the RV. For these purposes, RV lead 17 is equipped with pacing and sensing electrodes shown as a tip electrode 28 and a ring electrode 30. RV lead 17 is further shown to carry defibrillation electrodes 24 and 26, which may be elongated coil electrodes used to deliver high voltage cardioversion/defibrillation (CV/DF) pulses. Defibrillation electrode 24 may be referred to as the "RV defibrillation electrode" or "RV coil electrode" because it may be carried along RV lead 17 such that it is positioned substantially within the right ventricle when distal pacing and sensing electrodes 28 and 30 are positioned for pacing and sensing in the right ventricle. Defibrillation electrode 26 may be referred to as a "superior vena cava (SVC) defibrillation electrode" or "SVC coil electrode" because it may be carried along RV lead 17 such that it is positioned at least partially along the SVC when the distal end of RV lead 17 is advanced within the right ventricle.

Each of electrodes 24, 26, 28 and 30 are connected to a respective insulated conductor extending within the body of RV lead 17. The proximal ends of the insulated conductors are coupled to corresponding connectors carried by proximal lead connector 42, e.g., a DF-4 connector, for providing electrical connection to IMD 14. In other examples, RV lead 17 may carry RV coil electrode 24 and SVC coil electrode 26 to provide high voltage therapies without carrying any pacing and sensing electrodes 28 and 30. Housing 15 may function as an active electrode during CV/DF shock delivery in conjunction with RV coil electrode 24 or SVC coil electrode 26. In some examples, RV lead 17 is omitted from IMD system 10.

Housing 15 may function as a return electrode for unipolar sensing or pacing configurations with any of the electrodes carried by leads 16 and 18 (and RV lead 17 if present). As described herein, an electrode carried by His pacing and sensing lead 18, e.g., tip electrode 32, may be used in combination with housing 15 for receiving a far field cardiac electrical signal used in detecting capture following delivery of a His-Purkinje pacing pulse. Electrodes 32 and 34 are used in a bipolar sensing pair for receiving a near field His-Purkinje signal. IMD 14 is configured to produce a far field EGM signal and a near field EGM signal for processing and analysis performed to detect the capture type following a generated His-Purkinje pacing pulse.

It is to be understood that although IMD 14 is described as an implantable cardioverter defibrillator capable of delivering both low voltage cardiac pacing therapies and high voltage cardioversion and defibrillation (CV/DF) shocks, IMD 14 may be configured as a dual-chamber pacemaker in other examples coupled to only RA lead 16 and His pacing and sensing lead 18 without having CV/DF shock delivery capabilities and without being coupled to a third lead, such as RV lead 17. In still other examples, IMD 14 may be a single chamber pacing device with single chamber or dual chamber sensing. For example, IMD 14 may be coupled only to His pacing and sensing lead 18 for sensing cardiac electrical signals and delivering His-Purkinje pacing pulses for at least maintaining a minimum ventricular rate. His pacing and sensing lead 18 may carry additional sensing electrodes positioned within the RA when lead 18 is positioned for delivering His-Purkinje pacing pulses such that IMD 14 is capable of dual chamber (atrial and ventricular) sensing and delivery of atrial synchronized ventricular pacing.

An external device 50 is shown in telemetric communication with IMD 14 by a communication link 60. External device 50 may be embodied as a programmer used in a hospital, clinic or physician's office to retrieve data from IMD 14 and to program operating parameters and algorithms in IMD 14 for controlling IMD functions. External device 50 may alternatively be embodied as a home monitor or handheld device for retrieving data from IMD 14. External device 50 may be used to program cardiac signal sensing parameters, cardiac rhythm detection parameters, pacing and CV/DF therapy control parameters and capture detection control parameters used by IMD 14.

External device 50 may include a processor 52, memory 53, display unit 54, user interface 56 and telemetry unit 58. Processor 52 controls external device operations and processes data and signals received from IMD 14. Display unit 54, which may include a graphical user interface, displays data and other information to a user for reviewing IMD operation and programmed parameters as well as cardiac electrical signals retrieved from IMD 14. Data obtained from IMD 14 via communication link 60 may be displayed on display 54. For example, a clinician may view cardiac electrical signals received from IMD 14 and/or results of His capture threshold testing and monitoring or data derived therefrom. For example, processor 52 may generate a report of SHP, NSHP and VM capture thresholds based on capture threshold tests performed by IMD 14 for display to a user on display 54.

User interface 56 may include a mouse, touch screen, key pad or the like to enable a user to interact with external device 50 to initiate a telemetry session with IMD 14 for retrieving data from and/or transmitting data to IMD 14, including programmable parameters for controlling pacing capture determination and for setting His-Purkinje pacing pulse amplitude and pulse width. Telemetry unit 58 includes a transceiver and antenna configured for bidirectional communication with a telemetry circuit included in IMD 14 and is configured to operate in conjunction with processor 52 for sending and receiving data relating to IMD functions via communication link 60, which may include data relating to His-Purkinje system and ventricular myocardial capture management, such as capture thresholds determined for SHP capture, NSHP capture and VM capture. Thresholds or other parameters used for detecting SHP capture, NSHP capture and VM capture according to techniques disclosed herein may be programmed into IMD 14 using external device 50.

Communication link 60 may be established between IMD 14 and external device 50 using a wireless radio frequency (RF) link such as BLUETOOTH®, Wi-Fi, or Medical Implant Communication Service (MICS) or other RF or communication frequency bandwidth or communication protocols. Data stored or acquired by IMD 14, including physiological signals or associated data derived therefrom, results of device diagnostics, and histories of detected rhythm episodes, delivered therapies, and capture determinations may be retrieved from IMD 14 by external device 50 following an interrogation command.

Figure 1B:
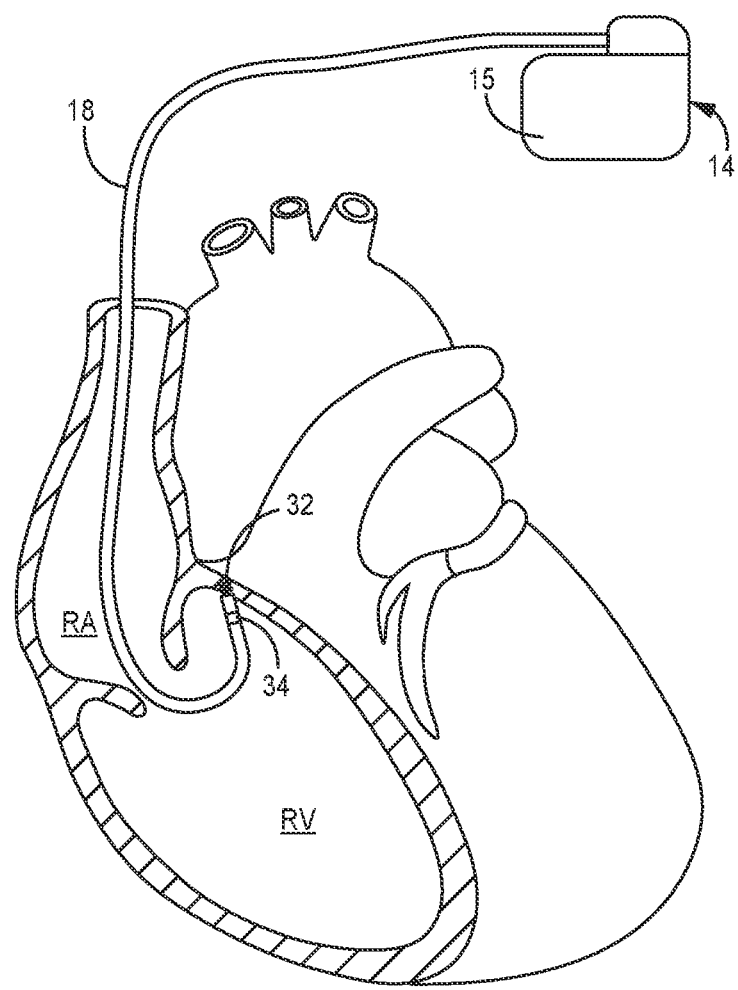
FIG. 1B is a conceptual diagram of an implantable medical device (IMD) coupled to a His pacing and sensing lead advanced to an alternative location in a patient's heart.

FIG. 1B is a conceptual diagram of an IMD 14 coupled to His pacing and sensing lead 18 advanced to an alternative location within the heart. In this example, the distal portion of His pacing and sensing lead 18 is advanced within the RV for sensing cardiac electrical signals and delivering pacing pulses to or in the vicinity of the His bundle. IMD 14 may be a single chamber device coupled only to His pacing and sensing lead 18 as shown. In other examples, IMD 14 may be a dual chamber device and be coupled to RA lead 16 as shown in FIG. 1A.

In this example, the tip electrode 32 is placed in or along the ventricular septal wall, e.g., high along the ventricular septal wall near the His bundle. Tip electrode 32 may be paired with the return anode ring electrode 34 for delivering His-Purkinje pacing pulses and for receiving raw near field cardiac signals that are used to produce a near field EGM signal, also referred to herein as a "near field cardiac electrical signal" or "near field His-Purkinje signal," that is analyzed for detecting capture type. The tip electrode 32 or the ring electrode 34 may be paired with IMD housing 15 for receiving a raw far field cardiac electrical signal that is used to produce a far field EGM signal, also referred to herein as a "far field cardiac electrical signal," and generate a differential signal from the far field EGM signal, both of which may be analyzed for determining capture type during His-Purkinje pacing according to the techniques disclosed herein.

Figure 2:
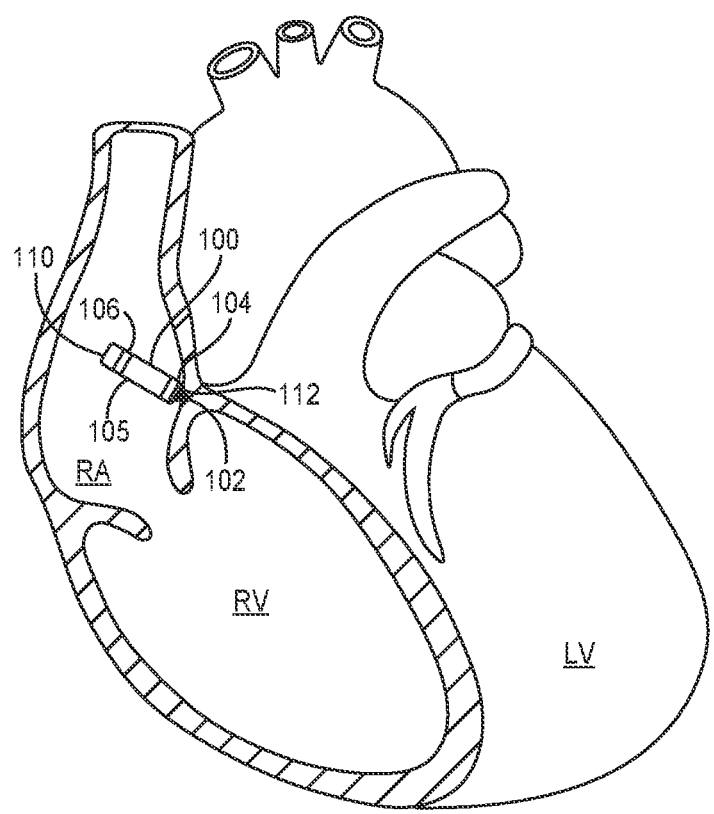
FIG. 2 is a conceptual diagram of a leadless intracardiac pacemaker positioned within the right atrium for providing His-Purkinje system pacing.

FIG. 2 is a conceptual diagram of a leadless intracardiac pacemaker 100 positioned within the RA for providing ventricular pacing via the His bundle. Pacemaker 100 may include a distal tip electrode 102 extending away from a distal end 112 of the pacemaker housing 105. Intracardiac pacemaker 100 is shown implanted in the RA of the patient's heart to place distal tip electrode 102 for delivering pacing pulses to the His bundle. For example, the distal tip electrode 102 may be inserted into the inferior end of the interatrial septum, beneath the AV node and near the tricuspid valve annulus to position tip electrode 102 in, along or proximate to the His bundle. In other examples, leadless intracardiac pacemaker 100 may be implanted within the right ventricle, e.g., high along the ventricular septum, for positioning distal tip electrode 102 in the vicinity of the His bundle or along the native His-Purkinje system. Distal tip electrode 102 may be a helical electrode providing fixation to anchor the pacemaker 100 at the implant position. In other examples, pacemaker 100 may include a fixation member that includes one or more tines, hooks, barbs, helices or other fixation member(s) that anchor the distal end of the pacemaker 100 at the implant site.

A portion of the distal tip electrode 102 may be electrically insulated such that only the most distal end of tip electrode 102, furthest from housing distal end 112, is exposed to provide targeted pacing at a tissue site that includes a portion of the His bundle. One or more housing-based electrodes 104 and 106 may be carried on the surface of the housing of pacemaker 100. Electrodes 104 and 106 are shown as ring electrodes circumscribing the longitudinal sidewall of pacemaker housing 105 extending from distal end 112 to proximal end 110. In other examples, a return anode electrode used in sensing and pacing may be positioned on housing proximal end 110. Pacing of the His-Purkinje system may be achieved using the distal tip electrode 102 as the cathode electrode and either of the housing-based electrodes 104 and 106 as the return anode.

Cardiac electrical signals produced by heart 8 may be sensed by pacemaker 100 using a sensing electrode pair selected from electrodes 102, 104 and 106. For example, a near field signal may be sensed using distal tip electrode 112 and distal housing-based electrode 104. A second cardiac electrical signal, which is a relatively more far-field signal, may be sensed using electrodes 104 and 106. The raw cardiac electrical signals may be processed by sensing and control circuitry included in pacemaker 100, e.g., as described below in conjunction with FIG. 3, for producing a near field His-Purkinje signal and a far field cardiac electrical signal. The near field and far field signals may be further processed and analyzed for determining capture type by discriminating between at least SHP capture, NSHP capture, VM capture and loss of capture.

Figure 3:
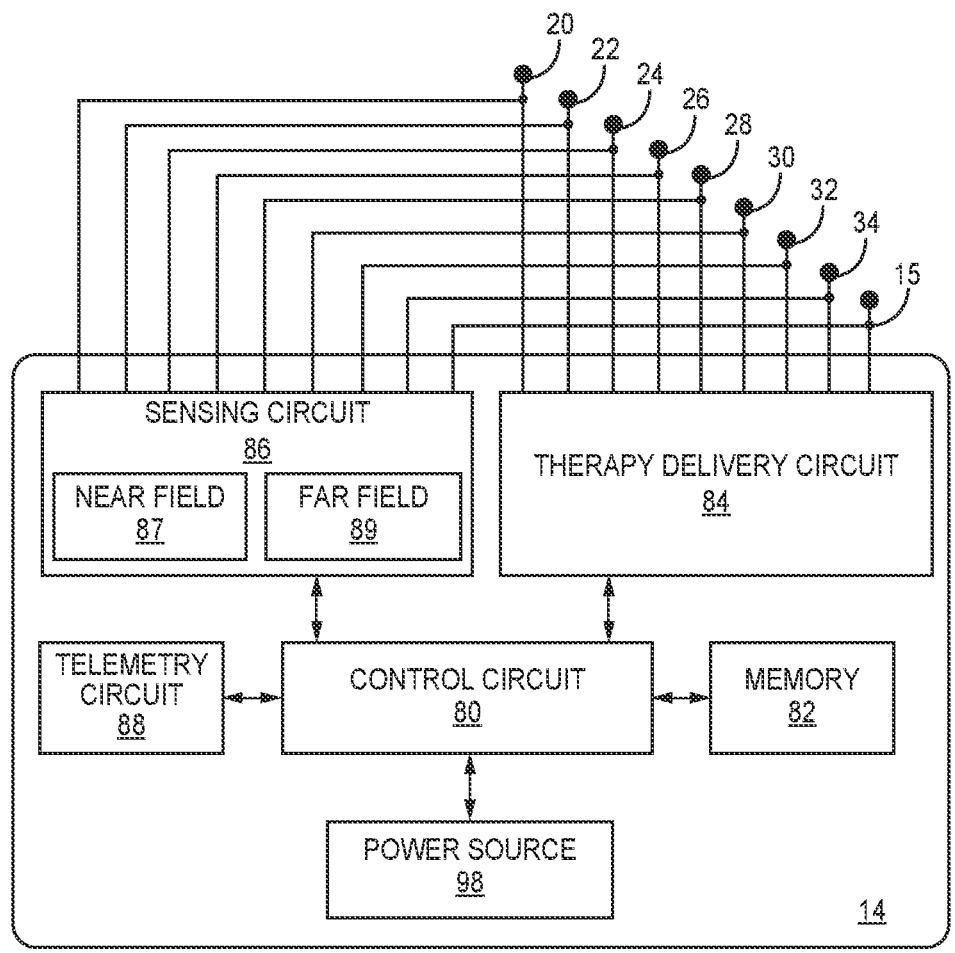
FIG. 3 is a schematic diagram of circuitry that may be enclosed within a medical device configured to perform His-Purkinje system pacing and capture detection according to the techniques disclosed herein.

FIG. 3 is a schematic diagram of circuitry that may be enclosed within a medical device configured to perform His-Purkinje pacing and capture detection using techniques disclosed herein. The block diagram of FIG. 3 is described with reference to IMD 14 coupled to electrodes carried by RA lead 16, RV lead 17 and His pacing and sensing lead 18 as shown in FIG. 1A for the sake of illustration, but it is to be understood that the functionality attributed to the various circuits and components shown in FIG. 3 for performing His-Purkinje pacing and detection and discrimination of SHP capture, NSHP capture, VM capture and loss of capture may be similarly implemented in the intracardiac pacemaker 100 of FIG. 2 or other medical device systems capable of delivering His-Purkinje pacing pulses and sensing cardiac electrical signals, e.g., including external pacemakers coupled to one or more transcutaneous medical electrical leads.

Housing 15 is represented as an electrode in FIG. 3 for use in cardiac electrical signal sensing and, in some examples, for delivery of cardiac electrical stimulation pulses such as unipolar pacing pulses or cardioversion/defibrillation shocks. The electronic circuitry enclosed within housing 15 includes software, firmware and hardware that cooperatively monitor cardiac electrical signals, determine when a pacing therapy is necessary, and deliver electrical pacing pulses to the patient's heart as needed according to programmed pacing mode and pacing pulse control parameters. The electronic circuitry includes a control circuit 80, memory 82, therapy delivery circuit 84, sensing circuit 86, telemetry circuit 88 and power source 98.

Power source 98 provides power to the circuitry of IMD 14 including each of the components 80, 82, 84, 86, and 88 as needed. Power source 98 may include one or more energy storage devices, such as one or more rechargeable or non-rechargeable batteries. The connections between power source 98 and each of the other components 80, 82, 84, 86, and 88 are to be understood from the general block diagram of FIG. 3 but are not shown for the sake of clarity. For example, power source 98 may be coupled to one or more charging circuits included in therapy delivery circuit 84 for providing the power needed to charge holding capacitors included in therapy delivery circuit 84 that are discharged at appropriate times under the control of control circuit 80 for delivering pacing pulses. Power source 98 is also coupled to components of sensing circuit 86, such as sense amplifiers, analog-to-digital converters, switching circuitry, etc., telemetry circuit 88 and memory 82 to provide power to the various components and circuits as needed.

The functional blocks shown in FIG. 3 represent functionality included in IMD 14 and may include any discrete and/or integrated electronic circuit components that implement analog and/or digital circuits capable of producing the functions attributed to IMD 14 (or pacemaker 100) herein. The various components may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. Providing software, hardware, and/or firmware to accomplish the described functionality in the context of any modern cardiac medical device system, given the disclosure herein, is within the abilities of one of skill in the art.

Control circuit 80 communicates, e.g., via a data bus, with therapy delivery circuit 84 and sensing circuit 86 for cooperatively sensing cardiac electrical signals and controlling delivery of cardiac electrical stimulation therapies in response to sensed cardiac events, e.g., P-waves attendant to atrial depolarizations and R-waves attendant to ventricular depolarizations, or the absence thereof. The available electrodes are electrically coupled to therapy delivery circuit 84 for delivering electrical stimulation pulses and/or to sensing circuit 86 for sensing cardiac electrical signals produced by the heart, including both intrinsic signals (such as intrinsic R-waves) produced by the heart in the absence of a pacing pulse that captures the heart and evoked response signals following a delivered pacing pulse of sufficient energy to cause capture.

Sensing circuit 86 may include two or more sensing channels for sensing raw cardiac electrical signals from two or more sensing electrode vectors. For example, a RA signal may be sensed using electrodes 20 and 22, an RV signal may be sensed using electrodes 28 and 30, and a near field His-Purkinje signal may be sensed using electrodes 32 and 34. As described below, a raw near field His-Purkinje signal may be sensed by one sensing channel, shown as near field sensing channel 87, for example using electrodes 32 and 34 of His pacing and sensing lead 18. A raw far field signal may be sensed by a second sensing channel, shown as far field sensing channel 89, using a second electrode vector having electrodes spaced further apart than the electrodes of the near field sensing electrode vector, e.g., using tip electrode 32 and housing 15.

As used herein, a "near field" signal refers to a cardiac electrical signal received from a sensing electrode vector including at least one electrode positioned at or proximate to the His bundle, at or in the vicinity of the site of His pacing pulse delivery, such that the near field signal may also be referred to as a "near field His-Purkinje signal." The near field His-Purkinje signal may or may not include a His-Purkinje evoked response signal depending on whether a delivered pacing pulse captured or not. The near field His-Purkinje signal may include an evoked response signal caused by SHP capture, an evoked response signal caused by NSHP capture or an evoked response signal caused by VM capture.

As used herein, a raw "far field" signal refers to a raw cardiac electrical signal received from a sensing electrode vector that is relatively further away from the His-Purkinje system than the electrode vector used to sense the raw near field His-Purkinje signal and/or has a greater inter-electrode distance between the two electrodes defining the far field sensing electrode vector than the inter-electrode distance between the two electrodes defining the near field His-Purkinje sensing electrode vector. A far field cardiac electrical signal produced from the raw far field signal by sensing circuit 86 may be more representative of the global activation of the ventricles as opposed to the near field signal being more representative of local tissue activation at or near the pacing site. The far field cardiac electrical signal may include an evoked response signal associated with SHP capture, NSHP capture or VM capture. Examples of differences in the evoked response signals of the near field and far field cardiac electrical signals during different capture types that may be determined and used by control circuit 80 for discriminating between capture types are discussed below in conjunction with FIGS. 5 through 8.

In examples presented herein, the raw near field His-Purkinje signal and the raw far field signal may be sensed using electrodes carried by His pacing and sensing lead 18 (FIGS. 1A and 1B) and IMD housing 15 or, in the example of FIG. 2, using only leadless, housing-based electrodes 104, 106 and 112. For example, the raw near field His-Purkinje signal may be sensed between His pacing lead electrodes 32 and 34, sometimes referred to as a "tip-to-ring" sensing electrode vector. The raw far field cardiac electrical signal may be sensed between His pacing lead tip electrode 32 and housing 15, sometimes referred to as a "tip-to-can" sensing electrode vector. A raw far field cardiac electrical signal may alternatively be sensed between the ring electrode 34 and housing 15.

In other examples, when additional leads and electrodes are available, the raw far field signal may be sensed using an electrode carried by RA lead 16 and the IMD housing 15, e.g., electrode 20 and housing 15 or electrode 22 and housing 15. In examples that include RV lead 17, the raw far field signal may be sensed using RV coil electrode 24 paired with housing 15, SVC coil electrode 26 paired with housing 15, or RV coil electrode 24 paired with SVC coil electrode 26.

Sensing circuit 86 may include switching circuitry for selectively coupling a near field sensing electrode pair from the available electrodes to the near field sensing channel 87 for sensing a raw near field His-Purkinje signal and for selectively coupling a far field sensing electrode pair to far field sensing channel 89 for sensing a raw far field signal that is "far field" relative to the site of delivering His-Purkinje pacing pulses. The far field sensing electrode pair may exclude at least one or both of the electrodes used to deliver the His-Purkinje pacing pulses. Switching circuitry may include a switch array, switch matrix, multiplexer, or any other type of switching device suitable to selectively couple components of sensing circuit 86 to selected electrodes.

Each of near field sensing channel 87 and far field sensing channel 89 may include an input filter for receiving a raw cardiac electrical signal from a respective pair of sensing electrodes, a pre-amplifier, an analog-to-digital converter and a bandpass filter for producing a multi-bit digital cardiac electrical signal, which may be referred to as an "EGM" signal when the raw signal is sensed from within a heart chamber, for use in detecting His-Purkinje capture and discriminating between any of SHP capture, NSHP capture, VM capture and loss of capture. Features of the near field and far field cardiac electrical signals produced by sensing circuit 86 may be determined by control circuit 80. As described below, control circuit 80 may include a software, firmware or hardware implemented differentiator for producing a differential signal from one or both of the near field His-Purkinje signal and the far field cardiac electrical signal for use in determining the type of capture following a His-Purkinje pacing pulse. Signal features may be determined from the filtered, amplified cardiac electrical signals without rectification in order to preserve the polarity and shape of the signal features. However, it is recognized that in some examples each sensing channel 87 and 89 may include a rectifier to produce a rectified signal for used in detecting intrinsic R-waves or pacing evoked responses. As described below in conjunction with FIGS. 5-8, features of the post-pace far field cardiac electrical signal and near field His-Purkinje signals following a His-Purkinje pacing pulse may be used to detect His-Purkinje pacing pulse capture and discriminate between different types of capture based upon features of the post-pace signal in the near field and far field signals. The post-pace signal following a His-Purkinje pacing pulse that captures the His-Purkinje system and/or the ventricular myocardium may also be referred to herein as an "evoked response signal" that is attendant to the evoked depolarizations caused by the pacing pulse, which may be sensed by sensing circuit 86.

As described below in conjunction with FIG. 4, sensing circuit 86 may include cardiac event detection circuitry, which may include one or more sense amplifiers, filters, rectifiers, threshold detectors, comparators, analog-to-digital converters (ADCs), timers or other analog or digital components, for detecting cardiac electrical events. For example, an atrial event detector may be included in sensing circuit 86 for detecting intrinsic P-waves attendant to intrinsic atrial depolarizations using one or both of electrodes 20 and 22 carried by RA lead 16. A ventricular event detector may be included in sensing circuit 86 for detecting intrinsic R-waves attendant to intrinsic ventricular depolarizations using electrodes 32 and 34 carried by His pacing and sensing lead 18 and/or using electrodes 24, 26, 28 and/or 30 carried by RV lead 17. A cardiac event sensing threshold, such as a P-wave sensing threshold or an R-wave sensing threshold, may be automatically adjusted by sensing circuit 86 under the control of control circuit 80, e.g., based on timing intervals and sensing threshold values determined by control circuit 80, stored in memory 82, and/or controlled by hardware, firmware and/or software of control circuit 80 and/or sensing circuit 86. The R-wave sensing threshold, for example, may be controlled to start at a starting threshold voltage following a post-ventricular blanking period then decrease according to a decay profile until reaching a minimum sensing threshold. The minimum R-wave sensing threshold may be set to a programmed sensitivity of the R-wave detection circuitry in the respective near field sensing channel 84 or in the far field sensing channel 89. The sensitivity, programmed to a voltage level typically in millivolts, is the lowest voltage level above which a cardiac event, an R-wave in this example, can be sensed by the cardiac event detection circuitry.

Upon detecting a cardiac electrical event based on a sensing threshold crossing, sensing circuit 86 may produce a sensed event signal that is passed to control circuit 80. For example, an atrial event detector may produce a P-wave sensed event signal in response to a P-wave sensing threshold crossing. A ventricular event detector may produce an R-wave sensed event signal in response to an R-wave sensing threshold crossing. The sensed event signals are used by control circuit 80 for setting pacing escape interval timers that control the basic time intervals used for scheduling cardiac pacing pulses. Control circuit 80 may include various timers or counters for counting down an atrioventricular (AV) pacing interval, a VV pacing interval, an AA pacing interval, etc. A sensed event signal may trigger or inhibit a pacing pulse depending on the particular programmed pacing mode. For example, a P-wave sensed event signal received from sensing circuit 86 may cause control circuit 80 to inhibit a scheduled atrial pacing pulse and schedule a His-Purkinje pacing pulse at the programmed AV pacing interval. If the AV pacing interval expires before control circuit 80 receives an R-wave sensed event signal from sensing circuit 86, therapy delivery circuit 84 may respond by generating and delivering a His pacing pulse at the AV pacing interval following the sensed P-wave and in this way deliver atrial-synchronized ventricular pacing. If an R-wave sensed event signal is received from sensing circuit 86 before the AV pacing interval expires, the scheduled His pacing pulse may be inhibited. The AV pacing interval controls the amount of time between an atrial event, paced or sensed, and a His-Purkinje pacing pulse to promote AV synchrony. A medical device capable of determining His-Purkinje pacing pulse capture type according to techniques disclosed herein may be configured for delivering ventricular bradycardia pacing therapy, atrial synchronized ventricular pacing, rate responsive pacing, cardiac resynchronization therapy (CRT), anti-tachycardia pacing therapy or other pacing therapies which may include pacing the ventricles via the His bundle.

Therapy delivery circuit 84 may include charging circuitry, one or more charge storage devices such as one or more holding capacitors, an output capacitor, and switching circuitry that controls when the holding capacitor(s) are charged and discharged across the output capacitor to deliver a pacing pulse to a selected pacing electrode vector coupled to the therapy delivery circuit 84. Therapy delivery circuit 84 may include one or more pacing channels. In the example of IMD 14, therapy delivery circuit 84 may include an RA pacing channel, a His pacing channel and an RV pacing channel each including one or more holding capacitors, one or more switches, and an output capacitor for producing pacing pulses delivered by the respective RA lead 16 (electrodes 20 and 22), RV lead 17 (electrodes 24, 26, 28 and 30) and His pacing and sensing lead 18 (electrodes 32 and 34). Charging of a holding capacitor to a programmed pacing voltage amplitude and discharging of the capacitor for a programmed pacing pulse width may be performed by therapy delivery circuit 84 according to control signals received from control circuit 80. For example, a pace timing circuit included in control circuit 80 may include programmable digital counters set by a microprocessor of the control circuit 80 for controlling the basic pacing time intervals associated with various single chamber or dual chamber pacing modes, CRT or anti-tachycardia pacing sequences. The microprocessor of control circuit 80 may also set the amplitude, pulse width, polarity or other characteristics of the cardiac pacing pulses, which may be based on programmed values stored in memory 82.

In some examples, IMD 14 may be configured to detect non-sinus tachycardia and deliver anti-tachycardia pacing (ATP). Therapy delivery circuit 84 may include high voltage therapy circuitry for generating high voltage shock pulses in addition to low voltage therapy circuitry for generating low voltage pacing pulses. In response to detecting atrial or ventricular tachycardia or fibrillation, control circuit 80 may control therapy delivery circuit 84 to deliver a CV/DF shock. The high voltage therapy circuitry may include high voltage capacitors and high voltage charging circuitry for generating and delivering CV/DF shock pulses using coil electrodes 24 and 26 and/or housing 15.

Control parameters utilized by control circuit 80 for sensing cardiac events and controlling pacing therapy delivery may be programmed into memory 82 via telemetry circuit 88. Telemetry circuit 88 includes a transceiver and antenna for communicating with an external device 50 (FIG. 1A) using radio frequency communication or other communication protocols as described above. Under the control of control circuit 80, telemetry circuit 88 may receive downlink telemetry from and send uplink telemetry to the external device 50. In some cases, telemetry circuit 88 may be used to transmit and receive communication signals to/from another medical device implanted in the patient.

Figure 4:
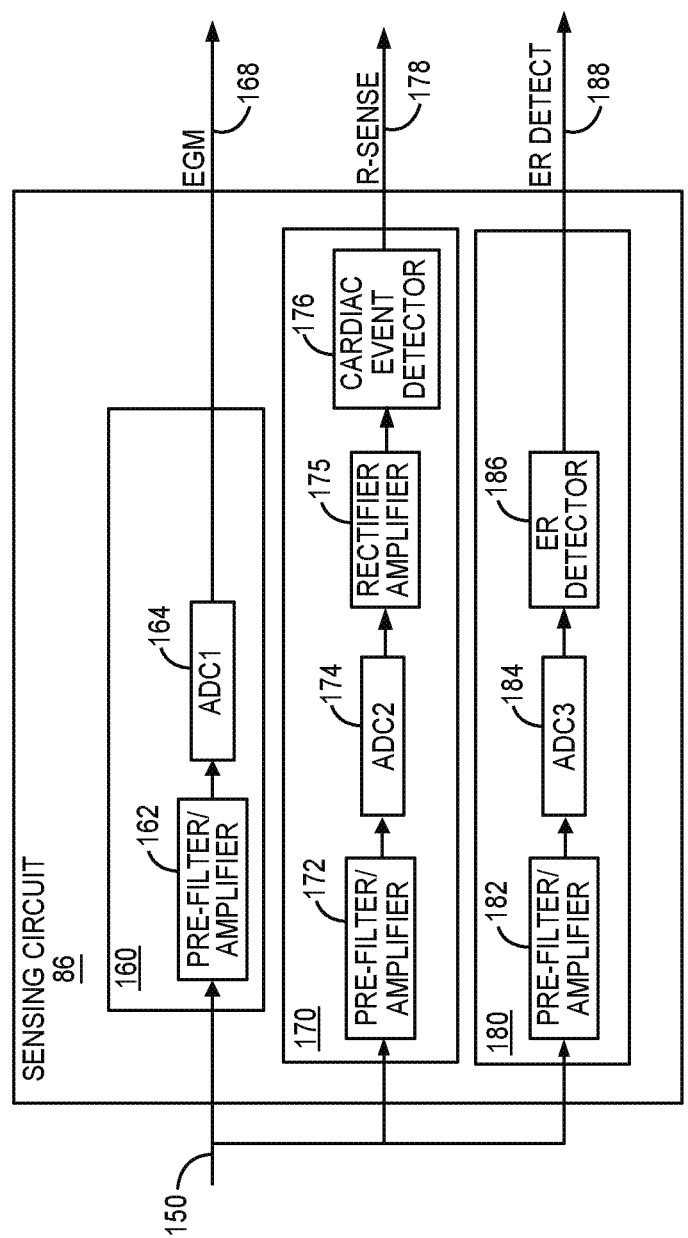
FIG. 4 is a schematic diagram of circuitry that may be included in the sensing circuit shown in FIG. 3.

FIG. 4 is a schematic diagram of circuitry that may be included in the sensing circuit 86 shown in FIG. 3. Each of the near field channel 87 and far field channel 89 (and any additional sensing channels included in sensing circuit 86 such as an RA channel), may include EGM signal circuit 160, cardiac event sensing circuit 170, and/or evoked response detection circuit 180. Accordingly, the circuits 160, 170 and 180 may represent components included in one of the near field channel 87 or the far field channel 89 shown in FIG. 3. As such, a raw input signal 150 sensed from a near field His-Purkinje sensing electrode pair or a far field sensing electrode pair may be received as input to each of the EGM signal circuit 160, the cardiac event sensing circuit 170 and the evoked response detection circuit 180.

The EGM signal circuit 160 may include a pre-filter and amplifier circuit 162 configured to receive the raw input signal 150 from a sensing electrode vector. In some examples, the EGM signal circuit 160 includes an analog filter and amplifier for producing a wide band filtered cardiac electrical signal, shown as output EGM signal 168, that is passed to control circuit 80. Pre-filter and amplifier circuit 162, which includes an analog filter in some examples, may have a relatively wide bandpass of 3 to 100 Hz for example. Analog-to-digital converter 164 (ADC1) may sample the wideband filtered signal at a desired sampling rate, e.g., 256 Hz, to produce the EGM signal 168 passed to control circuit 80. Depending on the sensing electrode vector selected to provide input signal 150, EGM signal 168 may be a far field cardiac electrical signal or a near field His-Purkinje signal, which may be further processed and analyzed by control circuit 80 according to the techniques disclosed herein for determining capture type following a His-Purkinje pacing pulse.

The input signal 150 received from a sensing electrode pair may also be received by cardiac event sensing circuit 170, shown including a pre-filter/amplifier 172, ADC2 174, rectifier/amplifier 175 and cardiac event detector 176. Pre-filter/amplifier 172 may include a relatively narrow band filter, which may be a digital filter, having a high pass frequency of 10 to 20 Hz and a low pass frequency of 40 to 60 Hz, as examples, for passing frequencies associated with intrinsic cardiac event signals, e.g., R-waves attendant to ventricular depolarization in the absence of a pacing pulse. The narrow-band filtered and sampled signal is passed to rectifier 175 from ADC2 174 to provide a rectified signal to a cardiac event detector 176, which may include a comparator, sense amplifier or other circuitry configured to detect an intrinsic R-wave (or a P-wave in the case of an atrial channel) that crosses an R-wave (or P-wave) sensing threshold. Cardiac event sensing circuit 170 produces a sensed cardiac event signal, shown in the example of FIG. 4 as an R-wave sensed event signal 178, which is passed to control circuit 80. As described above, control circuit 80 receives R-wave sensed event signals for use in determining the ventricular rate and controlling ventricular pacing.

In some examples, a sensing channel of sensing circuit 204 may include evoked response detection circuit 180. Evoked response detection circuit 180 may include a pre-filter/amplifier 182, ADC3 184 and evoked response (ER) detector 186 for producing an ER detect signal 188 that is passed to control circuit 80. The pre-filter/amplifier 182 may include a relatively wideband filter, which may be a digital filter, for passing an evoked response signal to ADC 3 184. The ER detector 186 receives the sampled, wideband filtered signal and compares the signal to an ER detection threshold amplitude during an ER window set in response to delivery of a His-Purkinje pacing pulse. When the wideband filtered signal crosses the ER detection threshold within the ER window, the ER detector 186 passes the ER detect signal 188 to control circuit 80. The ER window may extend, for example, 150 milliseconds (ms) to 180 ms after the His-Purkinje pacing pulse. The ER detection threshold may be about 0.5 to 1.5 millivolt, as an example. As disclosed herein, in response to receiving an ER detect signal 188 from sensing circuit 204, control circuit 80 may process and determine features of the EGM signal 168 for discriminating between SHP, NSHP and VM capture as described below.

In particular, the EGM signal 168 may be a non-rectified signal. When a His-Purkinje pacing pulse captures tissue at the pacing site and the His pacing and sensing tip electrode, e.g., electrode 32 in FIG. 1A, is used to sense the raw far field signal, the evoked response signal in the far field cardiac electrical signal has a negative polarity as the depolarization wavefront is traveling away from the sensing electrode positioned in the vicinity of the His-Purkinje pacing site. Accordingly, features of the EGM signal determined from the negative polarity portion of the evoked response signal may be determined and used in discriminating between capture types.

The circuitry shown in FIG. 4 may be included in each of the NF sensing channel 87 and the far field sensing channel 89. In some examples, only one of the near field channel 87 or the far field channel 89 includes cardiac event sensing circuit 170 for sensing R-waves. Only one of the near field channel 87 or the far field channel 89 may include ER detection circuit 180 for detecting evoked responses following His-Purkinje pacing pulses. In still other examples, ER detection circuit 180 may be omitted and control circuit 80 may be configured to compare EGM signal 168 (from either or both of the near field and/or far field channels 87 and 89) for detecting an evoked response based on an evoked response threshold crossing by the EGM signal within an ER window following a His-Purkinje pacing pulse. While EGM signal circuit 160, cardiac event sensing circuit 170, and evoked response detection circuit 180 are each shown as separate circuits it is to be understood that in some cases the EGM signal circuit 160, cardiac event sensing circuit 170, and/or evoked response detection circuit 180 may include some shared components, such as a shared filter, shared amplifier, shared ADC, shared rectifier or other components with an output signal of any shared components routed to the separate circuits 160, 170 and/or 180 as needed.

Figure 5:
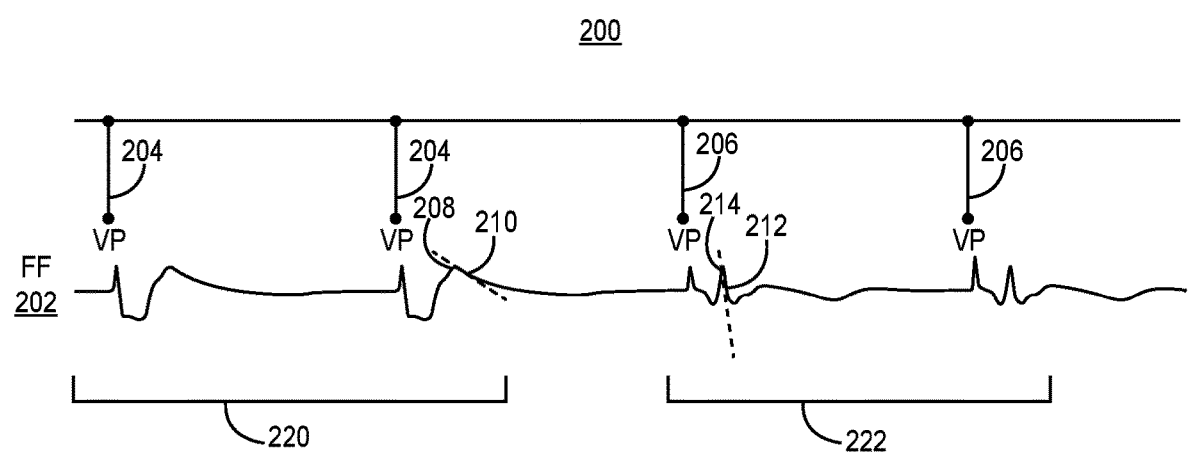
FIG. 5 is a timing diagram including a cardiac electrical signal and pacing pulse markers.

FIG. 5 is a timing diagram 200 including a far field (FF) cardiac electrical signal 202 pacing pulse markers 204 and 206 marking the time that a pacing pulse is delivered. The cardiac electrical signal 202 may correspond to a far field cardiac electrical signal produced from the raw signal received using at least one electrode located away from the His bundle and one electrode located at or near the pacing site. For example, far field cardiac electrical signal 202 may be produced from the raw signal sensed using tip electrode 32 of His pacing lead 18 positioned at or near the His-Purkinje system paired with the IMD housing 15 in the example of FIG. 1A or 1B or the tip electrode 112 and most proximal ring electrode 106 in the example of FIG. 2.

The delivered pacing pulse energy of a His-Purkinje system pacing pulse 204 or 206 may be adjusted by therapy delivery circuit 84, under the control of control circuit 80, e.g., by adjusting the pacing pulse amplitude and/or the pacing pulse width. The delivered pacing pulse energy depends on the pacing pulse amplitude, pacing pulse width, and lead and electrode impedance. In some examples, the pacing pulse width is set to a fixed value, e.g., 0.5 to 1 millisecond, and the pacing pulse amplitude is increased or decreased, e.g., between 0.25 and 8 Volts, to increase or decrease the pacing pulse energy to determine a capture threshold and set a pacing pulse energy to be a safety margin greater than a pacing capture threshold.

In FIG. 5, the first two ventricular pacing pulses 204 are delivered at a pacing pulse energy that results in NSHP capture 220. The second two pacing pulses 206 are delivered at a pacing pulse energy that results in SHP capture 222. The pulse energy of pacing pulses 204 may be greater than the pulse energy of pacing pulses 206 such that the NSHP capture threshold, which includes His-Purkinje capture and ventricular myocardial capture, is greater than the SHP capture threshold.

As observed from the far field cardiac electrical signal 202 in this example, the negative slope 212 following the maximum positive peak 214 in the evoked response signal during SHP capture 222 is steeper than the negative slope 210 following the maximum positive peak 208 in the evoked response signal during NSHP capture 220. This difference in the magnitude of the post-peak negative slopes 210 and 212 (following a maximum positive peak of the non-rectified evoked response signals in the far field cardiac electrical signal) may be used by control circuit 80 to distinguish SHP capture 222 from other types of capture, e.g., NSHP capture 220 as well as VM capture. For example, the absolute value of the magnitude of post-peak slopes 210 and 212 may be compared to a slope threshold by control circuit 80 for detecting SHP capture. When the absolute value of the post-peak slope 212 is greater than the slope threshold, SHP capture may be detected by control circuit 80. In some examples, control circuit 80 may adjust the pulse energy, e.g., by decreasing the pacing pulse amplitude, of His-Purkinje pacing pulses 204 and 206, until a threshold increase (in absolute value) in the post-peak slope is detected, indicating a change from NSHP capture to SHP capture. There may be other criteria required to be satisfied in combination with the post-peak slope threshold in order to detect SHP capture. In some examples, when the post-peak slope 210 is less than the slope threshold, SHP capture is not detected. Control circuit 80 may perform additional analysis of one or both of the far field signal 202 and near field His-Purkinje signal for determining the capture type as either NSHP capture or VM capture. In other examples, control circuit 80 may apply alternative SHP capture detection criteria for detecting SHP capture in response to the post-peak slope 210 being less than the slope threshold as described below in conjunction with FIG. 12.

Control circuit 80 may receive the far field cardiac electrical signal 202 from sensing circuit 86 and determine the post-peak slopes 210 and 212 by detecting the maximum positive peak 208 or 214 following delivery of a respective His-Purkinje pacing pulse 204 or 206 and determining the differences between succeeding far field signal sample points following the maximum peak 208 or 214, respectively. Control circuit 80 may step through consecutive or moving sets of sample points to determine a maximum difference between two sample points, which may be consecutive sample points or sample points that are a predetermined time interval or predetermined number of sample points apart, following the maximum positive peak 208 or 214. For example, the difference between the first and third sample points of three consecutive sample points, which may be sampled at 256 Hz, may be determined. Differences may be determined between the first and third sample points that occur a fixed number of sample points (or fixed time interval) following the maximum positive peak 208 or 214. In other examples, differences between alternating sample points for a predetermined number of sample points following the maximum positive peak 208 or 214 may be determined and a maximum difference is identified from among the determined differences. Alternatively, differences between selected sample points following maximum positive peak 208 or 214 may be determined until the difference is less than a low slope threshold (indicating a return to baseline). The maximum difference may then be identified and compared to a slope threshold for discriminating SHP capture and other types of capture.

In other examples, the difference between the amplitude of the maximum positive peak 208 or 214 and the amplitude of the nth sample point after the maximum positive peak may be determined. In some examples, a single slope is determined between predetermined sample points selected relative to the maximum positive peak 208 or 214 of the far field signal 202. In other examples, multiple post-peak sample point amplitude differences are determined, and a maximum difference is determined as the post-peak slope. The absolute value of the determined sample point amplitude difference (in volts) may be used as a metric of the post-peak negative slope and compared to a slope threshold in volts since the time interval between sample points used to determine the sample point amplitude difference may be fixed based on the sampling frequency, e.g., 256 Hz. In other examples, the post-peak slope may be determined as a change in amplitude over time (volts per millisecond) and compared to a slope threshold in volts per millisecond, for example.

Figure 6:
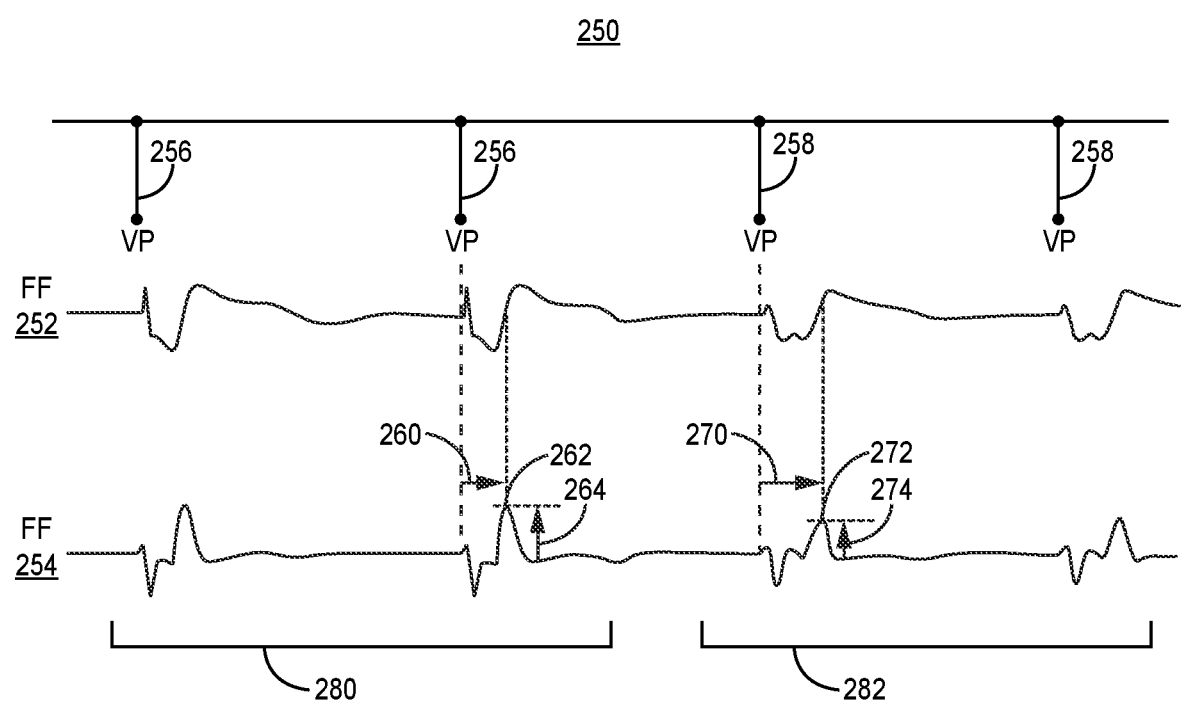
FIG. 6 is a diagram of a far field cardiac electrical signal and a differential signal generated from the far field cardiac electrical signal.

FIG. 6 is a diagram 250 of a far field cardiac electrical signal 252 produced by sensing circuit 86 (e.g., EGM signal 168) as described in conjunction with FIG. 4) and a differential signal 254 derived from the far field cardiac electrical signal 252. His-Purkinje pacing pulses 256 result in NSHP capture 280, and His-Purkinje pacing pulses 258, delivered at a lower pacing pulse energy (e.g., lower pulse amplitude) result in VM capture 282 (loss of His-Purkinje capture). The differential signal 254 may be derived from the far field signal 252 by control circuit 80. For example, control circuit 80 of FIG. 3 may include a low pass filter and a differential filter implemented in hardware, software or firmware. In one example, the far field cardiac electrical signal 252 is sampled at 256 Hz and passed through a low pass filter having an upper cut off frequency of 12 Hz. The low pass filter output may be determined from the equation $y(n)=x(n-1)+x(n)+y(n-1)-y(n-1)/4$ where $x(n)$ and $x(n-1)$ are the nth and nth−1 sample points of the far field cardiac electrical signal 252 and $y(n-1)$ is the preceding low pass filtered sample point.

The differential signal 254 may be determined using five consecutive sample points of the low pass filtered far field signal in one example. Each sample point of differential signal 254 may be determined using a five-point difference equation, e.g., $Z(n)=2*y(n-2)-y(n-1)+y(n+1)-2*y(n+2)$, though other coefficients and/or other number of sample points may be used to estimate a differential signal of the low pass filtered far field signal. It is further recognized that different filters or equations may be used when a different sampling rate is used other than 256 Hz as used in this is example.

The maximum positive peaks 262 and 272 of the differential signal 254 correspond to the maximum positive slope of the negative portion of the non-rectified evoked response signal. The maximum positive slope follows the minimum negative peak of the far field cardiac electrical signal 252. During NSHP capture 280, maximum positive peak 262 has amplitude 264 and occurs at a time interval 260 from the His-Purkinje pacing pulse 256. The maximum peak 272 of the differential signal 254 during VM capture 282 has a lower amplitude 274 and occurs at a longer time interval 270 from the corresponding His-Purkinje pacing pulse 258. One or both of these differences in maximum positive peak amplitudes 264 and 274 and/or maximum positive peak time intervals 260 and 270 of the far field differential signal 254, or a combination thereof, may be used as a metric for determining the type of capture following a His-Purkinje pacing pulse.

In some examples, the ratio of the maximum peak time interval (260 or 270) to the maximum peak amplitude (262 or 272, respectively) is determined as a capture discrimination metric for discriminating between NSHP capture 280 and VM capture 282. The ratio of NSHP capture maximum peak time interval 260 to maximum peak amplitude 264 is less than the ratio of the relatively longer VM maximum peak time interval 270 to relatively lower maximum peak amplitude 274. The maximum peak time interval 270 to amplitude 274 ratio is larger during VM capture 282 compared to NSBH capture 280 due to the delayed, lower amplitude maximum peak 272 following His-Purkinje pacing pulse 258, which fails to capture the His bundle. A higher maximum peak time to amplitude ratio is an indication of VM capture and a relatively low maximum peak time to peak amplitude ratio is an indication of capture of the His bundle, which may be NSHP capture.

The relatively shorter maximum peak time 260 may indicate improved conduction and pacing effectiveness associated with capture of the His-Purkinje system during NSHP capture 280. The combination of the two features of maximum peak time and maximum peak amplitude in a ratio of peak time to peak amplitude provides a metric derived from the negative portion of the evoked response signal in the far field cardiac electrical signal 252 that is a reliable discriminator between NSHP and VM capture. Examples presented herein describe techniques for generating a differential signal from the far field cardiac electrical signal for determining the maximum peak amplitude of the positive slope of the far field cardiac electrical signal and the maximum peak time interval to the maximum peak amplitude from the His-Purkinje pacing pulse. It is recognized that alternative techniques may be used for determining the maximum positive slope of the far field cardiac electrical signal and the corresponding time interval from the pacing pulse to the maximum positive slope for use in determining capture type and discriminating between VM and NSHP capture.

Figure 7:
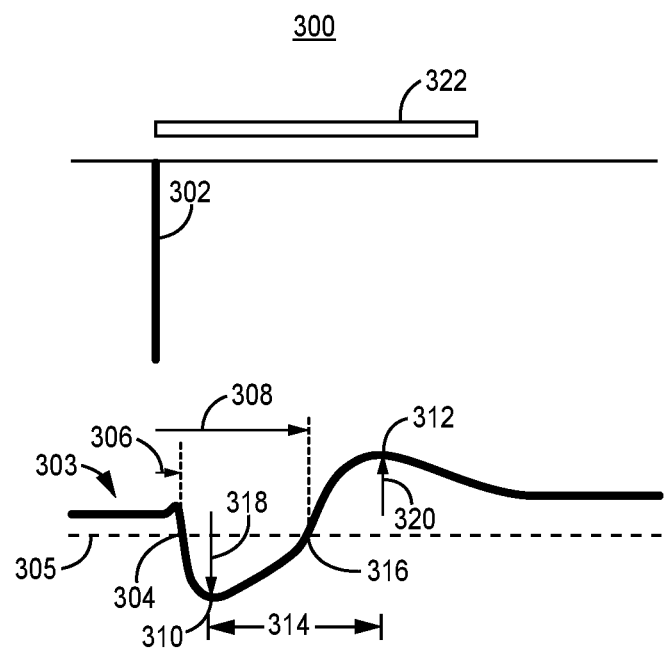
FIG. 7 is a diagram of a His bundle pacing pulse and the resulting far field cardiac electrical signal that may be produced by the medical device of FIG. 3.

FIG. 7 is a diagram 300 of pacing pulse 302 and resulting far field cardiac electrical signal 303 produced by sensing circuit 86. The far field cardiac electrical signal 303 is a non-rectified signal, e.g., EGM signal 168, received by control circuit 80 for determining signal features for discriminating between types of capture following a His-Purkinje system pacing pulse 302. A raw far field signal may be received by sensing circuit 86 via tip electrode 32 and housing 15, for example (see FIG. 1A or 1B), for producing far field cardiac electrical signal 303. The far-field cardiac electrical signal 303 is therefore produced from a raw cardiac electrical signal received using a His-Purkinje pacing electrode or another electrode if available at or near the pacing site such that the evoked response signal following pacing pulse 302 has a negative polarity due to the evoked depolarization traveling away from the electrode used to sense the raw far field signal.

Various features that may be determined by control circuit 80 include time intervals from the His-Purkinje pacing pulse 302 to a fiducial point of the far field cardiac electrical signal 303, amplitudes of fiducial points of the far field cardiac electrical signal 303 and/or slopes of the far field cardiac electrical signal 303. In the example shown, a first time interval 306 from the His-Purkinje pacing pulse 302 to a negative-going threshold crossing 304 and a second time interval 308 from His-Purkinje pacing pulse 302 to a positive going threshold crossing 316 may be determined. The threshold 305 may be a negative threshold value, e.g., −0.8 millivolts, to detect the start time 306 and the end time 308 of the negative depolarization portion of the evoked response signal. A third time interval 314 may be determined between the minimum negative peak 310 and the maximum positive peak 312. Time interval 314 is referred to herein as the "peak-to-peak time interval." Control circuit 80 may determine amplitude 318 of minimum peak 310 and amplitude 320 of maximum peak 312. As described above in conjunction with FIG. 5, the post peak slope may be determined as the maximum negative slope following maximum positive peak 312 and used as a capture discrimination feature.

Control circuit 80 may determine various features from the far field cardiac electrical signal 303 over a capture detection window 322 that is started upon delivery of His-Purkinje pacing pulse 302 and extends a predetermined time interval after pacing pulse 302, e.g., 220 ms. In some examples, each sample point of the far field cardiac electrical signal 303 is adjusted to account for baseline offset that may be caused by pacing pulse delivery. For example, the starting amplitude of far field cardiac electrical signal 303 at the onset of window 322, at the time of pacing pulse 302 delivery or just after, may be adjusted to zero millivolts to remove any voltage offset caused by pacing pulse delivery. Each subsequent sample point of far field cardiac electrical signal 303 during window 322 may be adjusted by the voltage offset. Control circuit 80 may perform this offset voltage adjustment to correct for a baseline shift prior to determining the far field signal features shown in FIG. 7.

Figure 8:
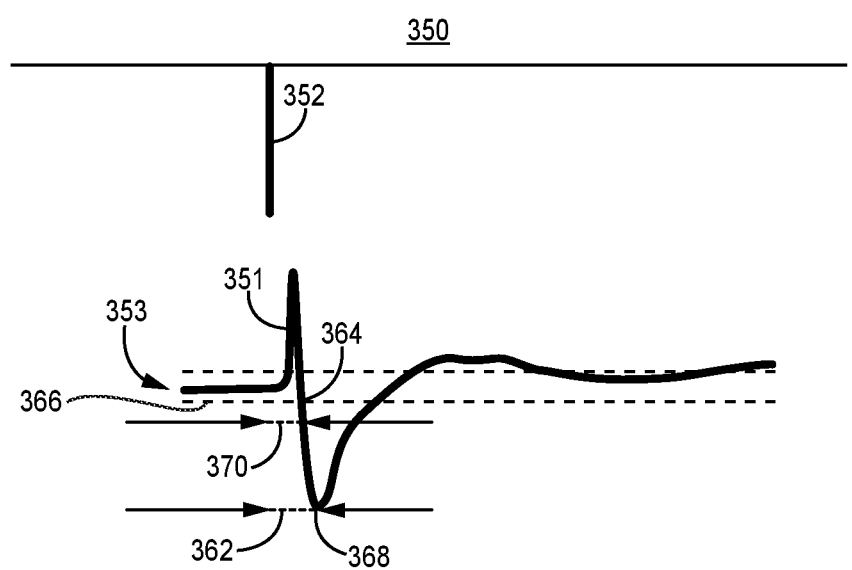
FIG. 8 is a diagram of a pacing pulse and subsequent near field His-Purkinje signal that may be produced by the medical device of FIG. 3.

FIG. 8 is a diagram 350 of a pacing pulse 352 and subsequent near field His-Purkinje signal 353, e.g., produced from a raw cardiac electrical signal acquired using His pacing tip electrode 32 and ring electrode 34 as shown in FIG. 1A or 1B. Control circuit 80 may determine various features of the near field His-Purkinje signal 353, also referred to herein as "near field cardiac electrical signal," for discriminating between capture types during His-Purkinje pacing. Among the features determined from the near field His-Purkinje signal 353 by control circuit 80 are time interval 362 from the His-Purkinje pacing pulse 352 to the absolute maximum peak 368 and time interval 370 from the His-Purkinje pacing pulse 354 to a threshold crossing 364 (which is negative in this example but may be positive in other examples). Threshold 366 may be set to a predefined value, e.g., −0.8 millivolts, and the time interval 370 may represent the "isoelectric distance" or time from the His-Purkinje pacing pulse until an electrical response to the pacing pulse is detected. The time intervals 362 and 370 may be used in verifying capture and discriminating between capture types. The early, narrow deflection 351, which may be positive or negative in various examples, is pacing artifact caused by delivery of pulse 352 and is ignored for the purposes of determining signal features and detecting capture and discriminating capture type.

As described below, a crossing 364 of threshold 366 by near field His-Purkinje signal 353 during a capture detection window 322 (shown in FIG. 7) may be used to confirm that loss of capture has not occurred in some examples. In response to threshold crossing 364, control circuit 80 may analyze the far field cardiac electrical signal, the near field His-Purkinje signal and/or the differential signal generated from the far field cardiac electrical signal for determining whether SHP, NSHP or VM capture has occurred in response to the His-Purkinje pacing pulse 352. For instance, the time intervals 370 and 362 may be compared to respective thresholds or ranges for verifying that the evoked response occurs within an expected time from pacing pulse 352 indicative of a particular capture type.

Figure 9:
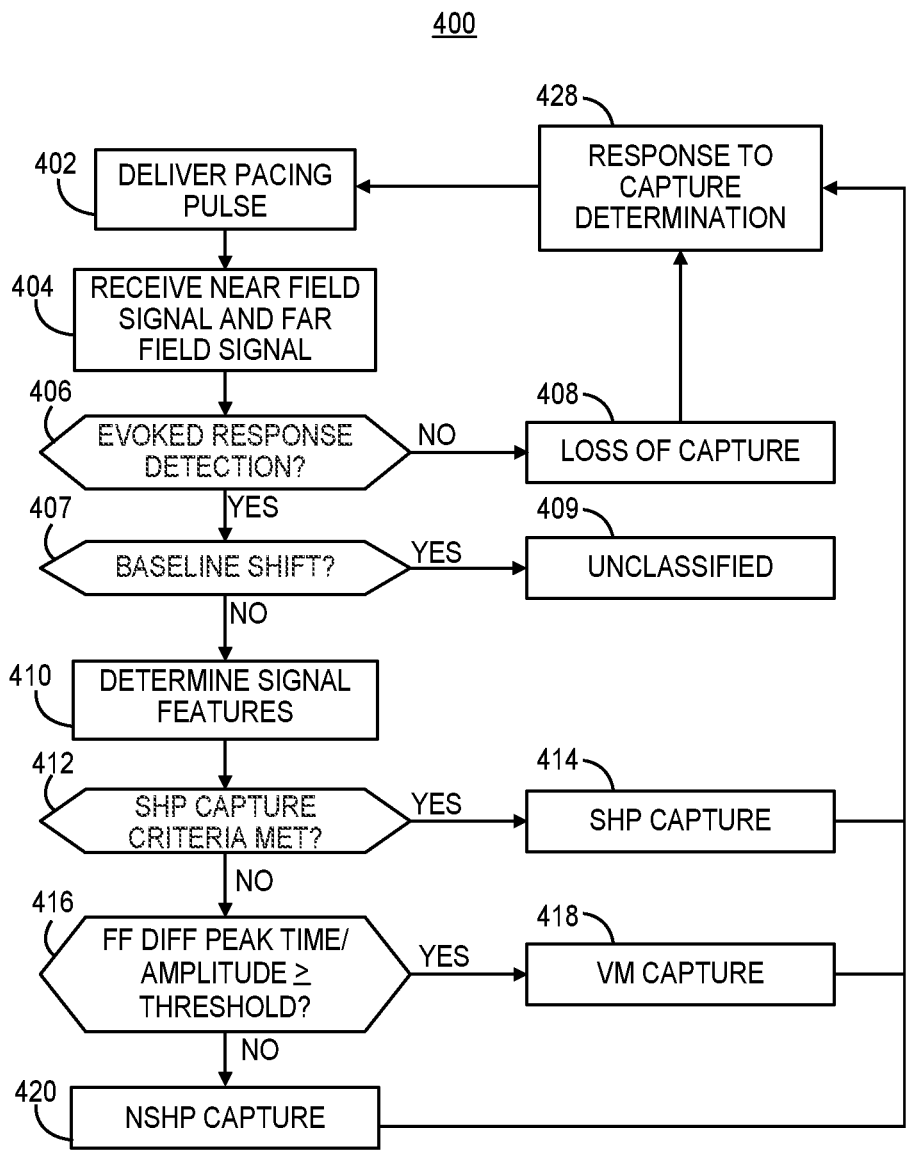
FIG. 9 is a flow chart of a method performed by a medical device for detecting capture during His-Purkinje system pacing according to one example.

FIG. 9 is a flow chart 400 of a method performed by a medical device, e.g., IMD 14 of FIG. 1A or 1B or pacemaker 100 of FIG. 2, for detecting capture during His-Purkinje system pacing according to one example. At block 402, a His-Purkinje pacing pulse is delivered. The His-Purkinje pacing pulse may be delivered as part of a capture threshold test. In this case, the pacing pulse delivered at block 402 may be one of a series of His-Purkinje pacing pulses delivered at different pacing pulse energies, e.g., by varying pulse amplitude. At other times, the His-Purkinje pacing pulse delivered at block 402 may be delivered as part of a ventricular pacing therapy, e.g., bradycardia pacing, atrial synchronized ventricular pacing, cardiac resynchronization therapy (CRT) or other pacing therapy. In this case, the process of flow chart 400 may be performed by the medical device for verifying capture of the His-Purkinje pacing pulse for managing and maintaining capture during the pacing therapy.

At block 404, control circuit 80 receives the near field His-Purkinje signal and the far field cardiac electrical signal from sensing circuit 86. Control circuit 80 may determine if an evoked response is detected at block 406. In some examples, sensing circuit 86 includes evoked response detection circuitry 180 (shown in FIG. 4) that produces an evoked response detect signal 188 passed to control circuit 80. In other examples, control circuit 80 may set a capture detection window, e.g., window 322 shown in FIG. 7, and detect an evoked response based on the amplitude of a received near field or far field EGM signal crossing the evoked response detection threshold during the capture detection window.

If the delivered energy of the pacing pulse is less than both the His-Purkinje system and the ventricular myocardial capture thresholds, no evoked response signal will be present during the capture detection window. For example, the amplitude of the near field or far field cardiac electrical signal will not cross the evoked response detection threshold indicating a relatively low amplitude baseline signal. The evoked response detection threshold crossing is used to discriminate loss of capture from capture, which may be any type of capture (e.g., SHP capture, NSHP capture or VM capture). As such, the evoked response threshold applied by control circuit 80 to an EGM signal may be set to a relatively small value, e.g., −0.8 millivolts, to detect the onset of the negative depolarization portion of an evoked response waveform. The evoked response detection threshold may be set higher or lower than the example of −0.8 millivolts, e.g., between −0.2 millivolts and −2.0 millivolts, and may be based on the evoked response signal strength and baseline noise in a given patient. The capture detection window may be 180 to 250 ms in duration, e.g., 220 ms, following the His-Purkinje pacing pulse.

If an evoked response is not detected ("no" branch of block 406), control circuit 80 detects loss of capture at block 408. In response to detecting the evoked response based on an EGM signal threshold crossing or receiving an evoked response detect signal from sensing circuit 86, control circuit 80 determines that capture has occurred and advances to block 410 for discriminating between capture types through analysis of the near field and far field cardiac electrical signals received from sensing circuit 86. When an evoked response is detected ("yes" branch of block 406), control circuit 80 may first check the near field and far field cardiac electrical signals received from sensing circuit 86 for baseline shift at block 407. A shift in the baseline of the near field or far field cardiac electrical signal may be caused by baseline drift or pacing artifact due to delivery of the His-Purkinje pacing pulse. Control circuit 80 may detect a baseline shift at block 407 based on a comparison of at least one signal sample point to a baseline amplitude range. For example, if a single sample point from the EGM signal corresponding in time to delivery of the His-Purkinje pacing pulse is outside the range of +0.8 millivolts, baseline shift is detected at block 407. The paced beat may be determined as "unclassified" at block 409. The detected evoked response may be caused by baseline shift or capture may have occurred but due to excessive baseline shift an analysis of evoked response signal features may be unreliable in determining the capture type. As such, the paced beat may be defined as unclassified at block 409 without performing additional cardiac electrical signal analysis.

When baseline shift is not detected at block 407, control circuit 80 advances to block 410 to determine near field signal and/or far field signal features for determining the detected capture type. Examples of features that may be determined at block 410 include any of those described above in conjunction with FIGS. 5 through 8. At block 412, control circuit 80 determines if criteria for detecting SHP capture are satisfied. Example techniques and criteria for detecting SHP capture are described below in conjunction with FIG. 12.

In one example, at least a post-peak slope is determined from the far field cardiac electrical signal at block 410. As shown and described in conjunction with FIG. 5, SHP capture may be distinguished from NSHP capture based on a relatively high post-peak slope following the maximum positive peak of the far field cardiac electrical signal. As such, control circuit 80 may at least detect the maximum positive peak of the far field signal at block 410 and determine a negative slope following the maximum positive peak as the post-peak slope, e.g., using any of the methods described in conjunction with FIG. 5. The determined post-peak slope may be compared to a slope threshold at block 412. If the (absolute) magnitude of the slope is greater than the slope threshold, indicating a relatively high slope ("yes" branch of block 412), SHP capture is detected at block 414. The slope threshold may be set to 1 millivolt in one example and the post-peak slope is required to be a negative slope. The slope may be determined as a voltage difference since the time interval between sample points is fixed for a given sampling rate. Consequently, the slope threshold may be defined in millivolts. Other criteria that may be applied at block 412 for detecting SHP capture are described in conjunction with FIG. 12 below.

When SHP capture detection criteria are not met ("no" branch of block 412), the capture type may be NSHP capture or VM capture. In order to discriminate between NSHP and VM capture, control circuit 80 may generate a far field differential signal from the far field cardiac electrical signal. Control circuit 80 determines one or both of the maximum positive peak amplitude of the far field differential signal and/or the maximum peak time interval from the His-Purkinje pacing pulse to the maximum positive peak amplitude of the far field differential signal. As described in conjunction with FIG. 6, control circuit 80 may determine the ratio of the maximum peak time interval to peak amplitude as a metric for discriminating between capture types. These features may be determined at block 410 or at block 416 in response to not detecting SHP capture at block 412. At least one of the peak amplitude, the peak time interval and/or the ratio of the peak time interval to the peak amplitude is/are compared to a respective threshold at block 416. When an evoked response is detected at block 406 and SHP capture is not identified based on SHP capture detection criteria being unmet, control circuit 80 may analyze the maximum peak time interval to peak amplitude ratio of the far field differential signal to discriminate between NSHP capture and VM capture (loss of His-Purkinje capture).

If the maximum peak amplitude is less than a respective threshold, the maximum peak time interval is greater than a respective threshold, and/or the peak time to peak amplitude ratio is greater than a ratio threshold, VM capture is indicated. In some examples, NSHP capture is detected at block 418 in response to the maximum peak time to peak amplitude ratio being less than or equal to a threshold ratio. If the ratio is greater than the ratio threshold, VM capture is detected at block 420. The ratio threshold may be set to a fixed ratio threshold or set based on a previously determined maximum peak time interval to amplitude ratio. A change in the ratio from a previously determined ratio indicates a change in capture type. As described below in conjunction with FIG. 10, a reference ratio may be determined during a known capture type and the ratio threshold may be set based on the reference ratio.

It is contemplated that other capture detection criteria may be applied at block 416 in addition to the maximum peak time interval to amplitude ratio threshold for detecting either VM capture or NSHP capture. For example, threshold criteria may be applied to any of the near field His-Purkinje signal features and/or far field signal features described above in conjunction with FIGS. 6 and 7. Such features may include features determined from the far field cardiac electrical signal such as the minimum peak amplitude 318, maximum peak amplitude 320, the peak-to-peak time interval 314 between the minimum peak 310 and maximum peak 312, negative depolarization start time determined as the time interval 306 from the His-Purkinje pacing pulse to a negative-going threshold crossing 304, negative depolarization end time determined as time interval 308 from the His-Purkinje pacing pulse to a positive going threshold crossing 316 of the negative portion of the evoked response signal, negative depolarization width between the negative-going threshold crossing 304 and positive-going threshold crossing 316 (all shown in FIG. 7) or any combination thereof. Features used to discriminate capture type may additionally or alternatively include features determined from the near field His-Purkinje signal such as the time interval 370 from the His-Purkinje pacing pulse to a negative going threshold crossing 364 and/or the time interval 362 from the His-Purkinje pacing pulse to a peak 368 as shown in FIG. 8. Methods for determining capture type, which include additional criteria based on time interval and/or amplitude features of the far field cardiac electrical signal and/or the near field His-Purkinje signal are described below in conjunction with FIGS. 11 and 12.

At block 428, control circuit 80 may perform a response to the determined capture type which may include storing the results of the capture determination in memory 82 and/or adjusting the His-Purkinje pacing pulse energy. When the method of flow chart 400 is being performed as part of a capture threshold test, control circuit 80 may store the capture type as being one of SHP, NSHP, VM or loss of capture, with the corresponding pacing pulse voltage amplitude (and/or width). Control circuit 80 may adjust the pacing pulse amplitude (and/or width) to a next test setting at block 428 and repeat the process of determining the capture type. This process may be repeated until at least one or all of the SHP capture threshold, NSHP capture threshold, and/or VM capture threshold is/are identified. Each capture threshold type may be identified as the lowest pacing pulse output setting, e.g., lowest pacing pulse amplitude for a given pulse width, at which the given type of capture is detected. Control circuit 80 may automatically set the pacing pulse amplitude (and/or width) to a safety margin above the determined capture threshold that includes capture of the His bundle, e.g., above the NSHP capture threshold or above the SHP capture threshold, to promote a high likelihood of capturing the His-Purkinje during a pacing therapy. In some examples, control circuit 80 reports the determined capture threshold(s) by storing the capture threshold data in memory 82 for transmission to external device 50 via telemetry circuit 88.

When the method of flow chart 400 is being performed for capture management during pacing therapy delivery, control circuit 80 may increase the pacing pulse amplitude (or width) at block 428 in response to detecting loss of capture (block 408) or in response to detecting VM capture (block 418) in order to increase the likelihood of capturing the His bundle. The loss of capture detections and/or VM capture detections and corresponding delivered pacing pulse energy may be logged in memory 82 at block 428 for use in identifying and tracking pacing capture thresholds and for determining the percentage of time that the patient is receiving effective His-Purkinje pacing therapy delivery.

In some examples, detection of NSHP capture or SHP capture may also trigger an adjustment of the pacing pulse energy when SHP or NSHP capture is preferred over the detected capture type. For example, if SHP capture is detected at block 414, control circuit 80 may increase the pacing pulse energy to achieve NSHP capture in order to achieve capture of both the His-Purkinje system and ventricular myocardial tissue to reduce the likelihood of total loss of ventricular capture. When NSHP capture is detected and SHP capture threshold is greater than the VM capture threshold, the pulse energy may be decreased at block 428 to achieve SHP capture without myocardial capture and to conserve power source 98.

In other examples, control circuit 80 may initiate a capture threshold test at block 428 in response to detection of loss of capture, detection of VM capture, or detection of one of SHP capture or NSHP capture when the other of NSHP or SHP capture is the preferred capture type. In these situations, control circuit 80 may be performing the method of FIG. 9 for capture monitoring during delivery of a pacing therapy and when the capture type is not the expected capture type, a capture threshold test may be performed by adjusting the pacing pulse energy to multiple pulse energy settings (e.g., multiple voltage amplitudes and/or pulse widths) to determine the capture threshold for one or more of SHP, NSHP and/or VM capture.

Figure 10:
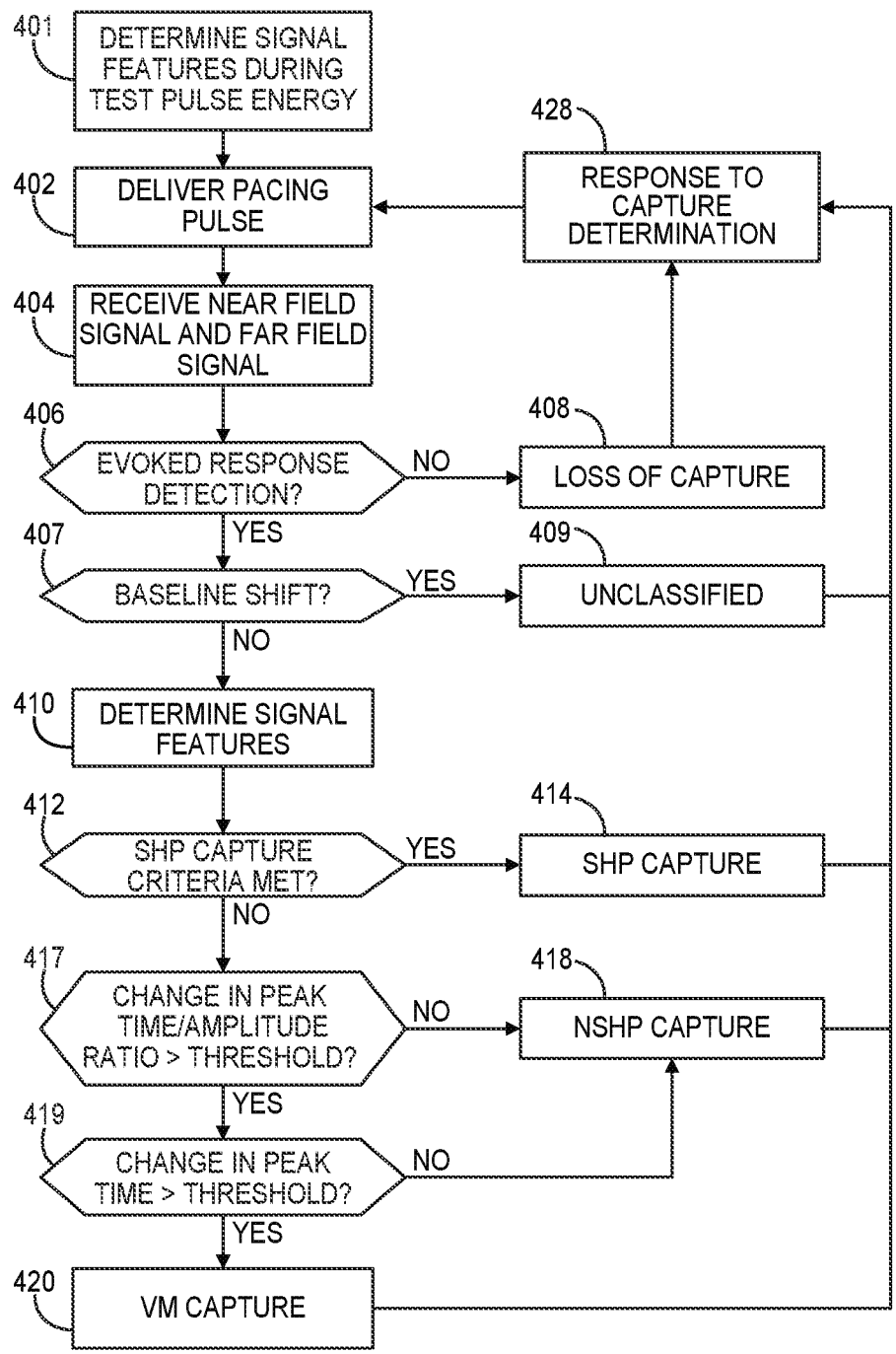
FIG. 10 is a flow chart of a method for determining capture type following delivery of a pacing pulse according to another example.

FIG. 10 is a flow chart 500 of a method for determining capture type following delivery of a pacing pulse according to another example. Identically numbered blocks in FIG. 10 correspond to like-numbered blocks in FIG. 9. In the process of flow chart 500, control circuit 80 establishes reference values of cardiac signal features during a known capture condition. For example, control circuit 80 may control therapy delivery circuit 84 to deliver a His-Purkinje pacing pulse at a test pulse energy at block 401 to establish reference values of cardiac electrical signal features. The test pulse energy may be selected to be a maximum test amplitude and pulse width setting, which may be equal to or less than the maximum available pacing pulse output settings of the medical device. In one example, the test pulse amplitude is set to 5 volts and the test pulse width is set to 0.5 to 1 millisecond pulse width.

This relatively high test pulse energy is expected to produce NSHP capture and therefore may be used to establish reference cardiac signal features for discriminating between SHP and NSHP capture and between VM and NSHP capture. In the case where NSHP capture is not achieved at the test pulse energy, the user may be able to program the type of capture observed at the test pulse energy or adjust the test pulse energy until NSHP capture is observed based on ECG or EGM signals. In other examples, the His-Purkinje pacing pulse amplitude and pulse width test setting used at block 401 may be selected to cause known VM capture or known SHP capture for use in establishing reference cardiac signal feature values corresponding to the respective capture type.

In the example of FIG. 10, at block 401, cardiac signal features are determined during the test pulse energy setting, which is expected to result in NSHP capture. As such, signal features determined at block 401 following one or more pacing pulses delivered at the test pulse energy are used to establish thresholds for discriminating NSHP capture from other types of capture. In one example, control circuit 80 generates the far field differential signal and determines the maximum positive peak amplitude and/or the time interval from the His-Purkinje pacing pulse to the maximum positive peak of the differential signal. In some examples, both the peak amplitude and peak time interval are determined, e.g., as described in conjunction with FIG. 6, so that control circuit 80 can determine and store the peak time to peak amplitude ratio in memory 82 as a reference ratio value for detecting capture that includes capture of the His bundle. This reference ratio value may be used for setting a threshold ratio for discriminating between NSHP and VM capture, e.g., after SHP capture is not detected based on other cardiac signal feature criteria.

At block 402, therapy delivery circuit 84 adjusts the pacing pulse energy to deliver a His-Purkinje pacing pulse according a capture threshold test or according to a pacing therapy being delivered. The near field His-Purkinje signal and far field cardiac electrical signal are produced by sensing circuit 86 and received by control circuit 80 at block 404. If an evoked response is detected by the evoked response detection circuit or based on a capture detection threshold crossing by the near field or far field cardiac electrical signals ("yes" branch of block 406), but the criteria for detecting SHP capture are not met ("no" branch of block 412), control circuit 80 may analyze the differential signal generated from the far field EGM signal at block 417. In some examples, the maximum peak time to peak amplitude ratio determined from the far field differential signal is determined at block 417. This ratio is compared to the reference ratio value determined at block 401 during a test His pacing pulse energy setting. When the ratio increases by a threshold amount, VM capture with a loss of His-Purkinje capture is indicated. In some examples, a change in the peak time to amplitude ratio indicating VM capture may be detected at block 417 in response to an increase of at least 20%, 30%, 50% or other predetermined percentage greater than the reference ratio value established at block 401. In response to a threshold increase in the maximum peak time to peak amplitude ratio, VM capture may be detected at block 420. When the change in this ratio is less than a threshold amount ("no" branch of block 417), NSHP capture is detected at block 418.

In some examples, additional criteria may be applied for discriminating between VM and NSHP capture. In the example of flow chart 500, at block 419 control circuit 80 compares the maximum positive peak time interval (from the His-Purkinje pacing pulse to the maximum positive peak of the far field differential signal) to the reference value established at block 401. Both the maximum peak time to peak amplitude ratio at block 417 and the maximum peak time at block 419 may be required to be increased by at least a threshold amount compared to the respective reference values established for a test pulse energy at block 401 in order to detect VM capture at block 420. Otherwise, NSHP capture is detected at block 418. As described above in conjunction with FIG. 9, control circuit 80 may perform an appropriate response to the determined capture type at block 428.

Figure 11:
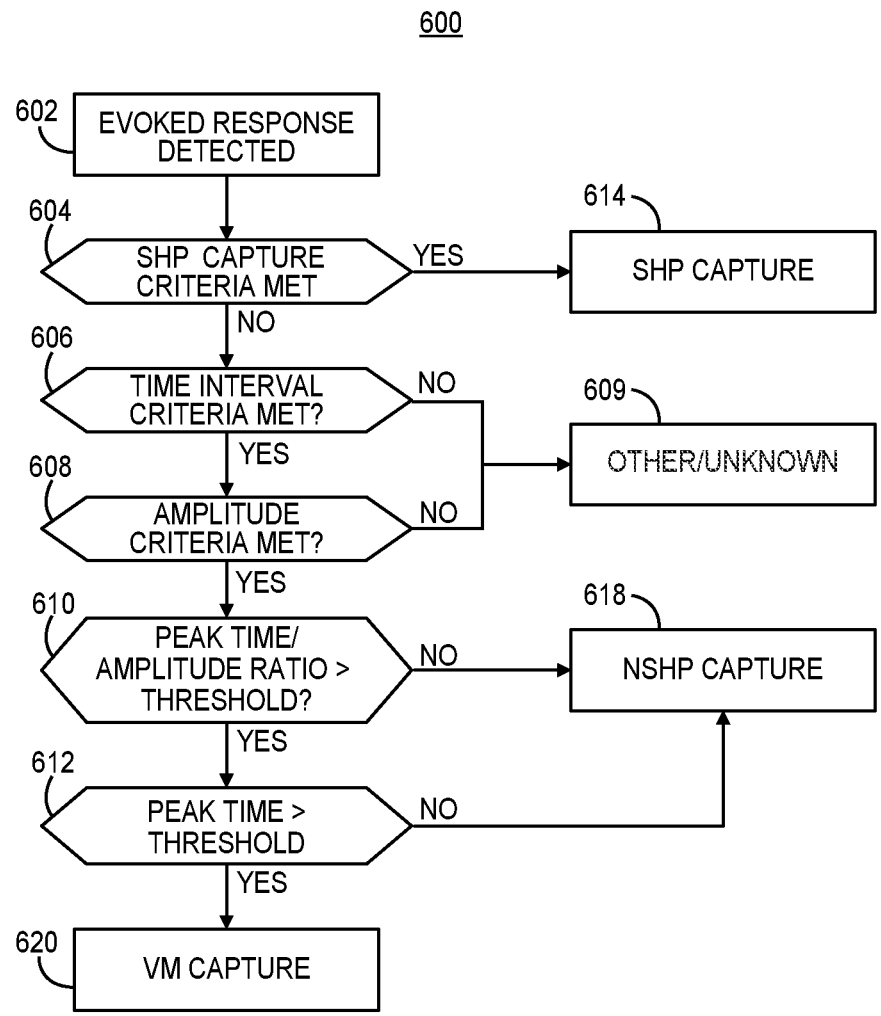
FIG. 11 is a flow chart of a method for detecting pacing capture type according to yet another example.

FIG. 11 is a flow chart 600 of a method for detecting pacing capture type according to another example. In response to detecting an evoked response signal following a His-Purkinje pacing pulse at block 602, control circuit 80 may determine if SHP capture detection criteria are met at block 604. It is recognized that in some examples, detecting an evoked response may be optional. SHP capture detection criteria may be applied to the near field His-Purkinje signal and/or far field cardiac electrical signal following a His-Purkinje pacing pulse at block 604. Example techniques for detecting SHP capture have been described above and are described below in conjunction with FIG. 12. When SHP capture detection criteria are unmet, control circuit 80 may determine whether time interval criteria for detecting capture that includes VM capture are met at block 606. Capture of myocardial tissue, with or without capture of the His bundle, is expected to produce a relatively early and wide evoked response signal. Accordingly, time interval features determined from the far field cardiac electrical signal, the near field cardiac electrical signal, and/or the differential signal generated from the far field cardiac electrical signal may be compared to threshold values at block 606 to determine that the time interval from the His-Purkinje pacing pulse to one or more signal features corresponds to an early and wide negative portion of the evoked response signal.

In one example, the time interval criteria applied at block 606 requires that one or more of the negative depolarization start time of the far field cardiac electrical signal, the negative depolarization end time of the far field cardiac electrical signal, and/or the peak-to-peak time interval of the far field cardiac electrical signal (e.g., from the negative minimum peak to the maximum positive peak) meet respective time interval thresholds. As described in conjunction with FIG. 7, the negative depolarization start time of the far field cardiac electrical signal may be determined as the time interval from the His-Purkinje pacing pulse to a negative-going, negative threshold crossing of the non-rectified evoked response signal. The negative depolarization end time of the far field cardiac electrical signal may be determined as the time interval from the His-Purkinje pacing pulse to a positive-going, negative threshold crossing of the non-rectified evoked response signal. The peak-to-peak time interval of the far field cardiac electrical signal may be the time interval from the negative, minimum peak to the maximum positive peak. These time intervals are polarity dependent in that the fiducial evoked response features or sample points defining the start time, end time and peak-to-peak time interval are each determined using a fiducial point of the negative polarity portion of the evoked response signal in the far field cardiac electrical signal.

The threshold criteria applied to each of the time intervals determined at block 606 are selected to differentiate between capture types and/or verify a physiological evoked response signal as opposed to non-cardiac noise or other artifact. In one example, the negative depolarization start time threshold is in the range of 80 ms to 100 ms, e.g., less than or equal to 94 ms. The negative depolarization end time threshold is in the range of 140 ms to 160 ms, e.g., less than or equal to 148 ms. The peak-to-peak time interval threshold may be defined as a range of at least 30 ms and not greater than 150 ms. A negative depolarization portion of the evoked response signal starting later or ending later than the respective threshold may be an indication of capture that does not include ventricular myocardial capture since the evoked depolarization of surrounding myocardial cells is not delayed due to conduction along the native conduction system. An evoked response signal having a peak-to-peak time interval that is greater than or less than the threshold range may be an indication of a fusion beat, possible far-field atrial P-wave oversensing or another event that is not an evoked response due to NSHP capture or VM capture. The time interval criteria applied at block 606 may additionally or alternatively require that the maximum positive peak time of the differential far field cardiac electrical signal be within a threshold range, e.g., at least 50 ms but not greater than 160 ms. The near field evoked response onset time may be required to be within a physiological capture window, e.g., within 80 ms of the His-Purkinje pacing pulse. An evoked response signal having an onset time in the near field His-Purkinje signal that is earlier than the threshold range may be noise, artifact, a fusion beat, a conducted atrial beat, an oversensed P-wave or another event that is not an NSHP or VM capture event. An evoked response signal having an onset time in the near field signal that is later than the threshold range may be indicative of atrial capture or other event that is not due to His-Purkinje or ventricular myocardial capture at the pacing site. When time interval criteria are unmet at block 606, control circuit 80 may identify the capture signal as an unknown or "other" capture type at block 609.

At block 608, amplitude criteria may be applied to the evoked response signal in the near field His-Purkinje signal, the far field cardiac electrical signal, and/or to the differential far field cardiac electrical signal. The amplitude criteria may be applied during the capture detection window. In some examples, the amplitude criteria may be included to eliminate signals that are not within a normal physiological range of an evoked response signal. In one example, the minimum peak amplitude 318 (see FIG. 7) of the far field cardiac electrical signal may be required to be greater than an amplitude threshold, e.g., greater than −7 millivolts. A minimum peak that is less than the amplitude threshold may be indicative of non-cardiac or non-physiologic artifact or other capture type, such as fusion of an evoked response and an intrinsic depolarization wavefront.

All or any combination of the time interval and amplitude criteria examples given above may be required to be satisfied in order to detect either NSHP or VM capture after SHP capture criteria are not met. If either of the time interval criteria and/or the amplitude criteria are not met, control circuit 80 may classify the detected capture as being an "other" capture type or unknown event at block 609.

When time interval and amplitude criteria are met, control circuit 80 may determine the peak time to peak amplitude ratio of the far field differential signal within the capture detection window. The peak time to peak amplitude ratio may be determined as described above in conjunction with FIG. 6. The peak time to peak amplitude ratio may be compared to a threshold value by control circuit 80 at block 610. The threshold value may be based on a reference ratio determined during His-Purkinje system pacing at a test pulse output setting for a known capture type. As described above in conjunction with FIG. 10, the reference ratio may be determined at a relatively high pacing pulse amplitude expected or confirmed to result in NSHP capture. If the peak time to peak amplitude ratio is not greater than a reference ratio or threshold based thereon, NSHP capture is detected at block 618. In addition to the ratio not increasing significantly from the reference ratio, control circuit 80 may compare the peak time interval of the far field differential signal (e.g., peak time interval 260 or 270 in FIG. 6) to the reference peak time interval or a threshold based thereon, determined during the test His-Purkinje pacing pulse output setting expected or confirmed to cause NSHP capture. If the peak time interval of the far field differential signal is not greater than the reference time interval or a threshold based thereon at block 612, NSHP capture may be detected at block 618. Otherwise, the capture type is identified by control circuit 80 as VM capture at block 620 in response to the peak time to peak amplitude ratio, and optionally the peak time interval, being greater than the respective reference ratio and reference peak time interval. As described above in conjunction with FIG. 9, block 428, control circuit 80 may perform a response to the determined capture type.

In the example of FIG. 10, SHP capture criteria are applied after detecting an evoked response and, when SHP capture criteria are not met, criteria for discriminating VM and NSHP capture are applied. It is contemplated, however, that the criteria relating to the far field differential signal peak time, peak amplitude, and/or peak time to peak amplitude ratio may be applied first to determine if VM capture is detected. If a change from the reference peak time, peak amplitude, and/or peak time to peak amplitude ratio is detected, control circuit 80 may detect VM capture and suspend any further cardiac electrical signal analysis. If VM is not detected, control circuit 80 may perform additional analysis to discriminate NSHP from SHP capture, e.g., by using the post-peak slope as shown in FIG. 5 and/or other criteria, e.g., as described below in conjunction with FIG. 12.

Figure 12:
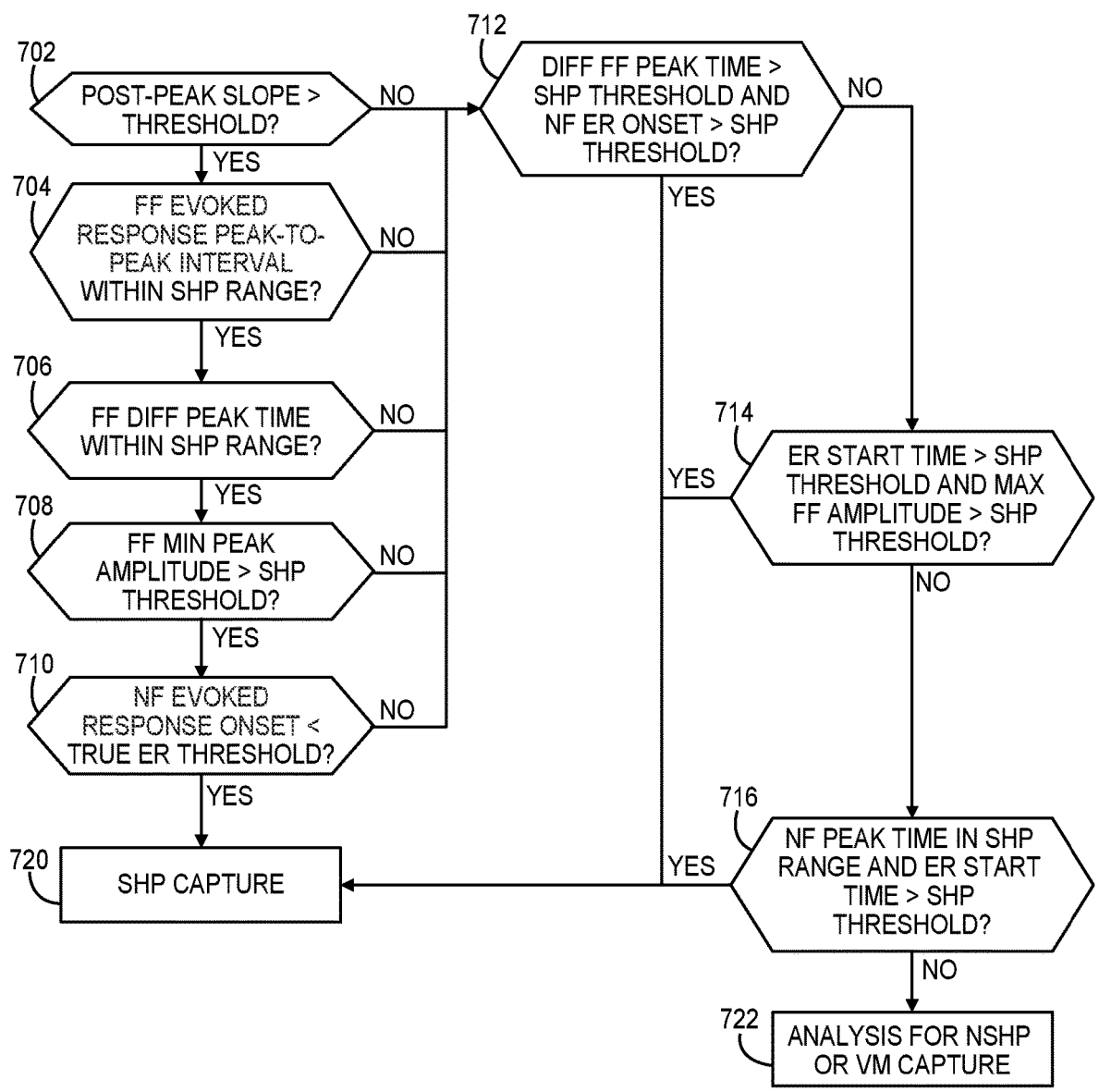
FIG. 12 is a flow chart of a method for detecting selective His-Purkinje system capture according to some examples.

FIG. 12 is a flow chart 700 of a method for detecting SHP capture according to one example. The method of flow chart 700 may be performed by control circuit 80 at block 412 of FIGS. 9 and 10 or block 604 of FIG. 11 to determine if SHP capture criteria are met. Multiple sets of SHP capture detection criteria may be applied with each set of criteria including one or more time interval requirements and/or one or more amplitude requirements. Each different set of SHP capture detection criteria may correspond to a different characteristic morphology of an evoked response signal that may occur in some patients during SHP. By applying multiple different combinations of SHP capture criteria, SHP capture may be reliably detected even when the evoked response signal morphology during SHP capture can vary between patients, electrode location, etc.

In one example, the post-peak slope of the far field cardiac electrical signal, following the maximum positive peak as shown in FIG. 5, may be compared to a slope threshold by control circuit 80 at block 702. If the absolute value of the maximum negative slope following the maximum positive peak is not greater than a slope threshold, an alternative set of SHP capture detection criteria are applied at block 712. If the post-peak slope meets the SHP threshold requirement at block 702, as described in conjunction with FIG. 5, additional time interval based and/or amplitude based criteria may be applied to detect one type of characteristic evoked response signal during SHP capture at blocks 704 through 710.

At block 704, the peak-to-peak time interval of the far field cardiac electrical signal (e.g., shown as time interval 314 in FIG. 7) is compared to a SHP threshold range. The peak-to-peak time interval is expected to be relatively narrow but wider than an artifact or noise spike that may be present in the far field signal. The maximum positive peak of the evoked response signal may occur earlier or later than the minimum negative peak of the evoked response signal depending on various factors. When the peak-to-peak time interval is defined as the time of the maximum positive peak to the time of the minimum negative peak, the difference is negative when the positive peak occurs earlier than the negative peak. The peak-to-peak time interval for SHP capture detection may therefore have a negative value. The peak-to-peak time interval may always be positive, however, during NSHP and RV capture. Accordingly, a threshold peak-to-peak time interval for SHP capture detection may be between −50 ms and +65 ms in one example. The peak-to-peak time interval in this case is determined as the time from the pacing pulse to the positive maximum peak minus the time from the pacing pulse to the negative minimum peak. If the peak-to-peak time interval of the far field cardiac electrical signal does not fall within the SHP capture detection threshold range, a different set of SHP capture detection criteria may be applied at block 712.

At block 706, the maximum positive peak time interval of the far field differential signal is compared to a SHP capture detection range by control circuit 80. The interval from the pacing pulse to the maximum peak of the far field differential signal may be outside the SHP capture detection range when myocardial capture is occurring, resulting in a longer peak time interval, or when another type of capture or noise is present in the far field cardiac electrical signal. The SHP capture detection threshold range applied to the peak time interval of the far field differential signal may be from 80 ms to 200 ms in one example.

When the far field differential signal peak time interval is within the SHP capture detection range ("yes" branch of block 706), control circuit 80 may compare the minimum peak amplitude of the far field cardiac electrical signal to a SHP capture detection threshold at block 708. The amplitude threshold for detecting SHP may be at least −7 millivolts in one example. This amplitude criterion may be applied to verify that that minimum peak is within a physiological range for an evoked response signal as opposed to other non-cardiac or non-physiological signal noise or artifact.

When the criteria applied at blocks 702, 704, 706, and 708 are satisfied, control circuit 80 may optionally verify that the time from the His-Purkinje pacing pulse to the onset of the evoked response in the near field EGM signal, e.g., time interval 370 in FIG. 8 which may be referred to as the "isoelectric distance," is within a threshold range, evidencing a true evoked response signal. The time interval to the onset of the evoked response signal in the near field His-Purkinje signal may be required to be greater than a minimum threshold time interval. For instance, the onset time interval may be required to be greater than 100 ms and less than 140 ms, as an example. A shorter time interval from the pacing pulse to the onset of the near field evoked response signal may indicate myocardium is captured and that analysis for NSHP or VM capture should be performed. A longer time interval may indicate that the signal is not a true evoked response signal. When the combination of criteria applied at blocks 702 through 710 are satisfied, SHP is detected by control circuit 80 at block 720 based on this first combination of SHP capture detection criteria.

This first set of criteria represented by blocks 702 through 710 may represent one type of evoked response signal that occurs with SHP. When any one of the criteria of blocks 702 through 710 are unmet, other combinations of criteria may be analyzed by control circuit 80 for still detecting SHP based on other characteristics of the SHP evoked response signals in the far field cardiac electrical signal, the far field differential signal and/or the near field His-Purkinje signal.

For instance, during SHP, the far field differential signal may have a delayed maximum positive peak time. This in combination with a relatively long near field evoked response onset may be adequate evidence for detecting SHP. The set of criteria applied at block 712 require that the positive peak time interval of the far field differential signal be greater than a respective SHP capture detection threshold and the onset of the evoked response signal in the near field His-Purkinje signal be greater than a respective SHP capture detection threshold. If these time intervals are greater than their respective thresholds, SHP capture may be detected by control circuit 80 at block 720. Example thresholds may be a far field differential signal peak time interval of at least 110 ms and the evoked response onset in the near field signal of at least 98 ms. If the peak time interval of the differential signal and the onset of the near field evoked response signal are both less than their respective thresholds, control circuit 80 may apply a third combination of SHP capture detection criteria at block 714.

At block 714, SHP capture may be detected when the evoked response start time 306 (FIG. 7) in the far field cardiac electrical signal is greater than a SHP capture detection threshold time and the maximum positive peak amplitude 320 (FIG. 7) of the far field cardiac electrical signal is greater than a SHP capture detection threshold amplitude. An example threshold for evoked response start time in the far field signal may be 80 ms, and an example amplitude threshold may be at least 1.5 millivolts. These criteria enable control circuit 80 to detect an evoked response signal during SHP capture that is characterized by a delay in the start of the evoked response due to conduction along the native conduction system. The positive peak amplitude of the evoked response signal in the far field signal may be required to be higher than a threshold amplitude to verify that the signal is a true evoked response signal.

If the criteria applied at block 714 are not satisfied, control circuit 80 may determine if an alternative combination of criteria for detecting SHP capture is satisfied at block 716. In this set of criteria, the peak time of the near field His-Purkinje signal (e.g., time interval 362 in FIG. 8 from the pacing pulse to the absolute maximum peak) may be required to be in an SHP time interval range, and the evoked response start time in the far field cardiac electrical signal (e.g., time interval 306 in FIG. 7) may be required to be greater than an SHP time interval threshold. For example, the near field peak time may be required to be in the range of at least 78 ms to less than 140 ms, and the evoked response start time in the far field signal may be required to be at least 40 ms in order to detect SHP capture.

When at least one of the combinations of SHP detection criteria applied at blocks 702 through 710, block 712, block 714 or block 716 is determined to be satisfied by control circuit 80, SHP capture is detected by control circuit 80 at block 720. Control circuit 80 may perform a response to the SHP capture determination as described above in conjunction with block 428 of FIG. 9. If none of the combinations of criteria applied for detecting SHP capture are satisfied, control circuit 80 advances to block 722 to perform additional analysis of the far field cardiac electrical signal, far field differential signal and/or near field His-Purkinje signal as described above in conjunction with FIG. 9, 10 or 11 for determining a different capture type.

Specific sets or combinations of example criteria are described in conjunction with FIG. 12 for detecting SHP capture when any one set or combination of criteria is satisfied. While specific examples are given, these examples are illustrative in nature. The near field and far field evoked response signals during SHP capture detection may present differently in different patients. By including multiple combinations of criteria for SHP capture detection, SHP capture may be detected when any one combination of criteria is satisfied. Within each combination of criteria, multiple criterion may each be required to be satisfied (e.g., according to a logical "AND"), but only one set or combination of criteria (e.g., according to a logical OR) out of the multiple combinations of criteria may be required to be satisfied to detect SHP capture. This is represented by the flow chart 700 of FIG. 12 where each requirement within a set of criteria, e.g., blocks 702 through 710, are all required to be satisfied for SHP capture to be detected, but, if not, one of the alternative sets of criteria (block 712 or block 714 or block 716) may be satisfied and lead to SHP capture detection. In this way, different combinations of near field, far field and/or far field differential signal features may define multiple combinations of criteria that indicate SHP capture to increase the sensitivity and specificity of SHP capture detection when variation in evoked response waveform morphology exists between patients and/or over time.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of circuits or components associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPLAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device, comprising:
  a sensing circuit configured to sense a cardiac electrical signal;
  a control circuit configured to:
    determine, from the cardiac electrical signal, at least an amplitude value of a maximum peak of a positive slope of the cardiac electrical signal; and
    determine a capture type of a pacing pulse as being one of non-selective His-Purkinje system capture or ventricular myocardial capture only without capture of the His-Purkinje system based on at least the amplitude value of the maximum peak of the positive slope of the cardiac electrical signal;
  a memory configured to store the determined capture type; and
  a therapy delivery circuit configured to generate at least one pacing pulse having a pacing pulse output based on the determined capture type.

2. The medical device of claim 1, wherein the control circuit is further configured to:
  determine a maximum peak time interval from the pacing pulse to the maximum peak of the positive slope; and
  determine the capture type of the pacing pulse as being one of non-selective His-Purkinje system capture or ventricular myocardial capture only without capture of the His-Purkinje system based on at least the amplitude value of the maximum peak of the positive slope of the cardiac electrical signal and the determined maximum peak time interval from the pacing pulse to the maximum peak amplitude of the positive slope.

3. The medical device of claim 2, wherein the control circuit is further configured to:
determine a ratio of the maximum peak time interval to the amplitude value of the maximum peak of the positive slope;
compare the ratio to a threshold ratio;
determine the capture type as non-selective His-Purkinje system capture in response to the ratio being less than or equal to the threshold ratio; and
determine the capture type as ventricular myocardial capture only without capture of the His-Purkinje system in response to the ratio being greater than the threshold ratio.

4. The medical device of claim 3, further comprising:
a therapy delivery circuit configured to deliver a test pacing pulse at a test pulse energy;
wherein the control circuit is configured to establish the threshold ratio by:
determining a reference maximum peak amplitude of a positive slope of the cardiac electrical signal and a reference maximum peak time interval from the test pacing pulse to the reference maximum peak amplitude;
determining a reference ratio of the reference maximum peak time interval to the reference maximum peak amplitude; and
establishing the threshold ratio based on the reference ratio.

5. The medical device of claim 1, wherein the control circuit is further configured to determine the amplitude value of the maximum peak of the positive slope by determining a maximum positive peak amplitude that corresponds to a maximum positive slope of a negative portion the cardiac electrical signal.

6. The medical device of claim 1, wherein the control circuit is configured to:
determine at least one evoked response signal feature from the cardiac electrical signal;
compare the at least one evoked response signal feature to a selective His-Purkinje system capture threshold requirement;
responsive to the at least one evoked response signal feature meeting the selective His-Purkinje system capture threshold requirement, detect selective His-Purkinje system capture by a pacing pulse; and
responsive to the at least one evoked response signal feature not meeting the selective His-Purkinje system capture threshold requirement, analyze the cardiac electrical signal for determining the capture type of the pacing pulse as being one of non-selective His-Purkinje system capture or ventricular myocardial capture only without capture of the His-Purkinje system.

7. The medical device of claim 1 wherein the control circuit is further configured to control the therapy delivery circuit to generate pacing pulses according to a capture threshold test in response to determining the capture type as being ventricular myocardial capture only without capture of the His-Purkinje system.

8. A method, comprising:
sensing a cardiac electrical signal by a sensing circuit of a medical device;
determining at least an amplitude value of a maximum peak of a positive slope of the cardiac electrical signal;
determining a capture type of a pacing pulse as being one of non-selective His-Purkinje system capture or ventricular myocardial capture only without capture of the His-Purkinje system based on at least the amplitude value of the maximum peak of the positive slope of the cardiac electrical signal;
storing the determined capture type in a memory of the medical device; and
generating at least one pacing pulse having a pacing pulse output based on the determined capture type.

9. The method of claim 8, further comprising:
determining a maximum peak time interval from the pacing pulse to the maximum peak of the positive slope; and
determining the capture type of the pacing pulse as being one of non-selective His-Purkinje system capture or ventricular myocardial capture only without capture of the His-Purkinje system based on at least the amplitude value of the maximum peak of the positive slope of the cardiac electrical signal and the determined maximum peak time interval from the pacing pulse to the maximum peak of the positive slope.

10. The method of claim 8, further comprising:
determining a ratio of the maximum peak time interval to the amplitude value of the maximum peak of the positive slope;
comparing the ratio to a threshold ratio;
determining the capture type as non-selective His-Purkinje system capture in response to the ratio being less than or equal to the threshold ratio; and
determining the capture type as ventricular myocardial capture only without capture of the His-Purkinje system in response to the ratio being greater than the threshold ratio.

11. The method of claim 10, further comprising:
delivering a test pacing pulse at a test pulse energy;
establishing the threshold ratio by:
determining a reference maximum peak amplitude of a positive slope of the cardiac electrical signal and a reference maximum peak time interval from the test pacing pulse to the reference maximum peak amplitude;
determining a reference ratio of the reference maximum peak time interval to the reference maximum peak amplitude; and
establishing the threshold based on the reference ratio.

12. The method of claim 8, further comprising determining the amplitude value of the maximum peak of the positive slope by determining a maximum positive peak amplitude that corresponds to a maximum positive slope of a negative portion the cardiac electrical signal.

13. The method of claim 8, further comprising
determining at least one evoked response signal feature from the cardiac electrical signal;
comparing the at least one evoked response signal feature to a selective His-Purkinje system capture threshold requirement;
responsive to the at least one evoked response signal feature meeting the selective His-Purkinje system capture threshold requirement, detecting selective His-Purkinje system capture by a pacing pulse; and
responsive to the at least one evoked response signal feature not meeting the selective His-Purkinje system capture threshold requirement, analyzing the cardiac electrical signal for determining the capture type of the pacing pulse as being one of non-selective His-Purkinje system capture or ventricular myocardial capture only without capture of the His-Purkinje system.

14. The method of claim 8, further comprising generating pacing pulses according to a capture threshold test in response to determining the capture type as being ventricular myocardial capture only without capture of the His-Purkinje system.

15. A non-transitory, computer-readable storage medium comprising a set of instructions which, when executed by a controller of a medical device cause the medical device to:
sense a cardiac electrical signal by a sensing circuit of a medical device;
determine at least an amplitude value of a maximum peak of a positive slope of the cardiac electrical signal;
determine a capture type of a pacing pulse as being one of non-selective His-Purkinje system capture or ventricular myocardial capture only without capture of the His-Purkinje system based on at least the amplitude value of the maximum peak of the positive slope of the cardiac electrical signal;
store the determined capture type in a memory of the medical device; and
generate at least one pacing pulse having a pacing pulse output based on the determined capture type.

16. A medical device, comprising:
a sensing circuit configured to sense a cardiac electrical signal;
a control circuit configured to:
determine at least one evoked response signal feature from the first cardiac electrical signal by:
identifying a maximum positive peak of the first cardiac electrical signal; and
determining an amplitude value of a post-peak slope of the first cardiac electrical signal following the maximum positive peak;
compare the amplitude value of the post-peak slope to a slope threshold;
determine a capture type of a pacing pulse as being selective His-Purkinje system capture in response to the amplitude value of the post-peak slope being greater than the slope threshold;
a memory configured to store the determined capture type of the pacing pulse; and
a therapy delivery circuit configured to generate at least one pacing pulse having a pacing pulse output based on the determined capture type.

17. The medical device of claim 16, further comprising a therapy delivery circuit configured to generate pacing pulses; and
the control circuit is further configured to control the therapy delivery circuit to generate at least one pacing pulse based on the determined capture type.

18. The medical device of claim 16, wherein the therapy delivery circuit is further configured to generate pacing pulses each having a pacing pulse energy; and
the control circuit is further configured to control the therapy delivery circuit to increase the pacing pulse energy in response to the determined capture type.

* * * * *